(12) United States Patent
O'Brien et al.

(10) Patent No.: US 8,609,819 B2
(45) Date of Patent: Dec. 17, 2013

(54) EXTRACELLULAR SERINE PROTEASE

(75) Inventors: Timothy J O'Brien, Little Rock, AR (US); Lowell J Underwood, Little Rock, AR (US); John Beard, Little Rock, AR (US); Kazushi Shigemasa, Minami-ku (JP)

(73) Assignee: Board of Trutees of the University of Arkansas, Little Rock, AK (US)

( * ) Notice: Subject to any disclaimer, the term of this patent is extended or adjusted under 35 U.S.C. 154(b) by 0 days.

(21) Appl. No.: 13/486,011

(22) Filed: Jun. 1, 2012

(65) Prior Publication Data

US 2012/0264123 A1 Oct. 18, 2012

Related U.S. Application Data

(60) Division of application No. 12/802,335, filed on Jun. 4, 2010, now Pat. No. 8,216,794, which is a division of application No. 10/652,846, filed on Aug. 29, 2003, now Pat. No. 7,732,163, which is a continuation-in-part of application No. 09/796,294, filed on Feb. 28, 2001, now Pat. No. 7,157,084, which is a continuation-in-part of application No. 09/618,259, filed on Jul. 18, 2000, now Pat. No. 6,642,013, which is a continuation-in-part of application No. 09/137,944, filed on Aug. 21, 1998, now Pat. No. 7,067,250, which is a continuation-in-part of application No. 08/915,659, filed on Aug. 21, 1997, now Pat. No. 7,014,993.

(51) Int. Cl.
| | |
|---|---|
| *C07K 16/00* | (2006.01) |
| *C07K 16/40* | (2006.01) |
| *C07K 16/30* | (2006.01) |
| *C07K 16/46* | (2006.01) |
| *C12P 21/08* | (2006.01) |
| *C12N 9/00* | (2006.01) |
| *G01N 33/53* | (2006.01) |

(52) U.S. Cl.
USPC .............. 530/387.1; 530/387.3; 530/388.1; 530/388.26; 530/391.1; 530/391.7; 435/975

(58) Field of Classification Search
None
See application file for complete search history.

(56) References Cited

U.S. PATENT DOCUMENTS

| | | | | |
|---|---|---|---|---|
| 5,945,294 | A * | 8/1999 | Frank et al. | 435/7.9 |
| 6,100,059 | A * | 8/2000 | Southan et al. | 435/69.1 |
| 6,203,979 | B1 * | 3/2001 | Bandman et al. | 435/6.16 |
| 6,303,318 | B1 * | 10/2001 | O'Brien | 435/7.1 |
| 6,603,318 | B2 * | 8/2003 | Hansen et al. | 324/689 |
| 6,642,013 | B1 * | 11/2003 | O'Brien et al. | 435/7.24 |
| 7,014,993 | B1 * | 3/2006 | O'Brien et al. | 435/6.16 |
| 7,067,250 | B1 * | 6/2006 | Underwood et al. | 435/6.16 |
| 7,157,084 | B2 * | 1/2007 | O'Brien et al. | 424/94.64 |
| 7,537,901 | B2 * | 5/2009 | Underwood et al. | 435/7.1 |
| 7,732,163 | B2 * | 6/2010 | O'Brien et al. | 435/69.1 |
| 8,216,794 | B2 * | 7/2012 | O'Brien et al. | 435/7.1 |

FOREIGN PATENT DOCUMENTS

WO  WO 99/09138  *  9/1999

OTHER PUBLICATIONS

Yu et al, Investigative Ophthalmology & Visual Science 49(2): 522-527, Feb. 2008.*
Witte et al, Cancer and Metastasis Reviews 17: 155-161, 1998.*

* cited by examiner

*Primary Examiner* — Phuong Huynh
(74) *Attorney, Agent, or Firm* — Benjamin Aaron Adler

(57) ABSTRACT

The present invention provides a DNA encoding a novel extracellular serine protease termed Tumor Antigen Derived Gene-14 (TADG-14) which is overexpressed in ovarian, breast and colon carcinoma samples. Also provided are vector and host cells capable of expressing the DNA of the present invention, as well as the uses of the DNA and protein of the present invention. Also provided is a TADG-14 protein variant that has a potential role for detecting and targeting of ovarian carcinomas.

10 Claims, 14 Drawing Sheets

1: normal ovary  2: tumor
3: normal ovary  4: tumor

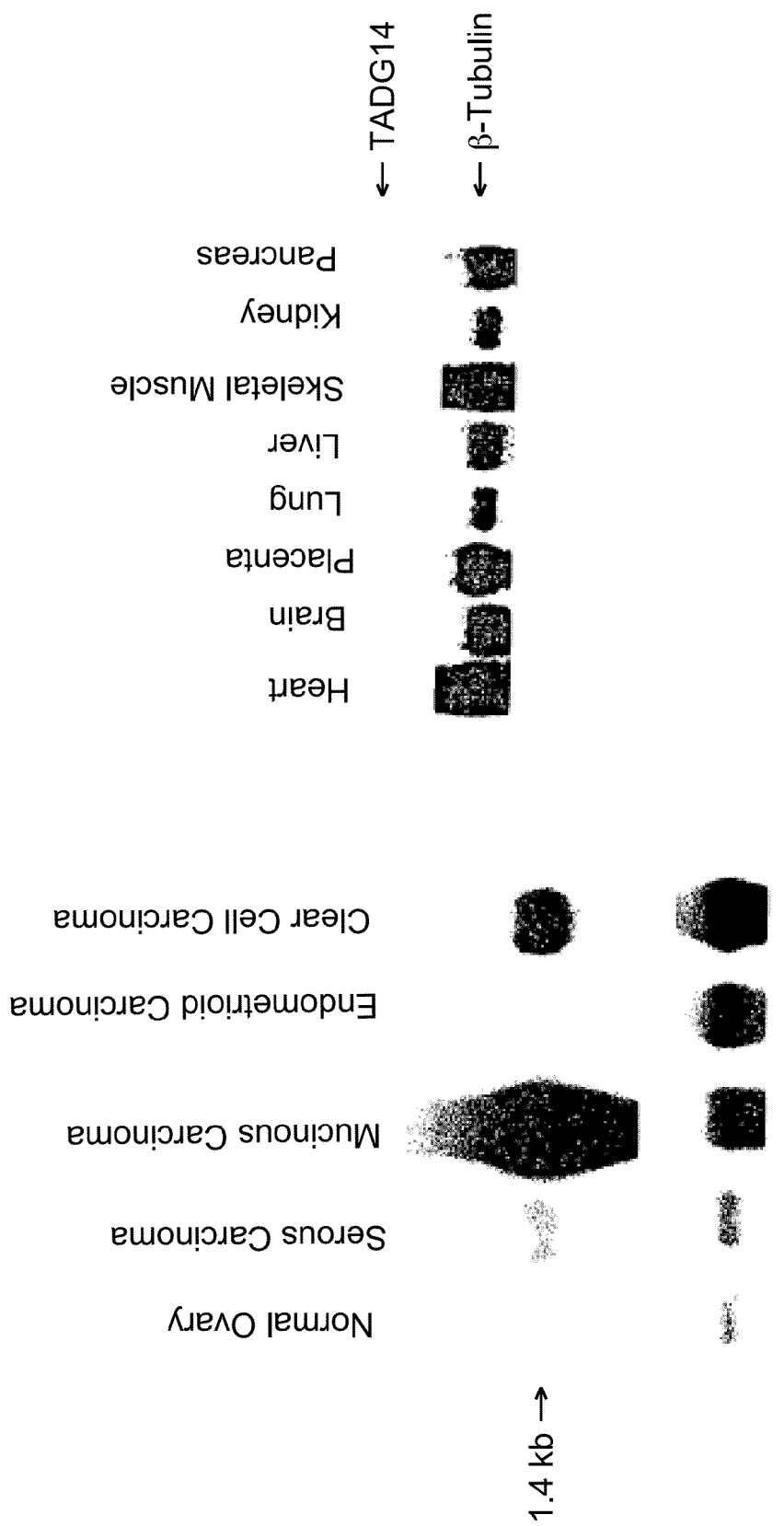

```
   1 CTGTAGCAGGCAGAGCTTACCAAGTCTCTCCGAACTCAAATGGAAGAAATACCTTATGAATGTAAGAATGTAGGGGGTCA    80
  81 TGGCTTGTAATTTACACAGTGTAAATGAAACCATCTAGAGAATTATGAGGAATCCTTTCTATGTGATTTCAATCATAG    160
 161 CAAGCAAGAAAAGGCTCCAGTGTTCAGTCTTCAAGGTAGTTCAGCTCTTCAAAATCAGTAGACATTTCTTGGACATAAAACAGTCCATACTTGAGAGAAAACTTA    240
 241 GATCTGAGTGATGAAGTGACGTAATCACCATTGGTCAGTGGGAAAACTAAGGGCCTCCAACAGGCAAATTCAGGGAGGATAGT    320
 321 CTTCAAATTGAGAAGTTACGTAATCCCAATTACACATTGGTCAGTGGGAAAACTAAGGGCCTCCAACAGGCAAATTCAG    400
 401 GTATAGCTTTGAATCCCAATTACACATTGGTCAGTGGGAAAACTAAGGGCCTCCAACAGGCAAATTCAGGGAGGATAGT    480
 481 TTCAGGGAATGCCCTGGATTCTGAAGACCTCACCATGGGACGCCCCCGTGCGGCCAAGACGTGGATGTTCCTG    560
         M  G  R  P  R  A  A  K  T  W  M  F  L
 561 CTCTTGCTGGGGGAGCCTGGGCAGGACACTCCAGGGACGAGGACAAGGTGCTGGGGGTCATGAGTGCCAACCCA    640
      L  L  L  G  G  A  W  A  G  H  S  R  A  Q  E  D  K  V  L  G  G  H  E  C  Q  P  H
 641 TTCGCAGCC[TTGGCAGGGCGGCCTTGTTCCAGGGCAACTACTCTGTGGCGGTCCTCTTGTAGTTGGCAACTGGTCC    720
      S  Q  P  W  Q  A  A  L  F  Q  G  Q  L  L  C  G  G  V  L  V  G  N  W  V  L
 721 TTACAGCTGCCCACT]GTAAAAAACCGAAATACACAGTACGCCTGGAGACCACAGCTCTACAGAATAAAGATGGCCCAGAG    800
      T  A  A  H  C  K  K  P  K  Y  T  V  R  L  G  D  H  S  L  Q  N  K  D  G  P  E
 801 CAAGAAATACCTGTTGGTTCAGTCCATCCATACAACAGCAGCGATGTGGAGGACCACAACCAT[GATCTGAT    880
      Q  E  I  P  V  V  Q  S  I  P  H  P  C  Y  N  S  S  D  V  E  D  H  N  H  D  L  M
 881 GCTTC]TTCAACTGCGTGACCAGGACCATCCTGGGGTCCAAAGTGAAGCCCATCAGCCTGGCAGATCATTGCACCCAGCCTG    960
      L  Q  L  R  D  Q  A  S  L  G  S  K  V  K  P  I  S  L  A  D  H  C  T  Q  P  G
 961 GCCAGAAGTGCACCGTCTCAGGCTGGGGCACTGTCACCAGTCCCCGAGAGAATTTCCTGACACTCTCAACTGTGCAGAA    1040
      Q  K  C  T  V  S  G  W  G  T  V  T  S  P  R  E  N  F  P  D  T  L  N  C  A  E
1041 GTAAAAATCTTTCCCCAGAAGAAGTGTGAGGATGCTTACCCGGGGCAGATCACAGATGGCATGGTCTGTGCAGGCAGCAG    1120
      V  K  I  F  P  Q  K  K  C  E  D  A  Y  P  G  Q  I  T  D  G  M  V  C  A  G  S  S
1121 CAAAGGGGCTGACACGTGCCAGGGCGATTCTGAGGCCCCCCTGGTCTGTGATGGTGCACTCCAGGGCATCACATCCTGGG    1200
      K  G  A  D  T  C  Q  G  D  S+ G  P  L  V  C  D  G  A  L  Q  G  I  T  S  W  G
1201 GCTCCAGACCCCTGTGGGAGGTCCGACAAACCTGCGTCTATACCAACATCTGCCGCTACCTGGACTGGATCAAGAAGATC    1280
      S  D  P  C  G  R  S  D  K  P  G  V  Y  T  N  I  C  R  Y  L  D  W  I  K  K  I
1281 ATAGGCAGCAAGGGCTGATTCTAGGATAAGCACTAGATCTCCCTTAATAAACTCACGGAATTC    SEQ ID NO. 7
      I  G  S  K  G  *  SEQ ID NO. 6
```

*italics* = Kozak's Consensus sequence and bold = Poly – adenylation signal
\+ = Conserved amino acids of catalytic triad H, D, S
NSS = Possible N – linked glycosylation site;
☐ = Conserved nt of catalytic triad
bold= aa required for formation of an oxyanion hole for catalytic activity
FLLLL = secretion signal sequence

FIG. 3A

```
hHk2      ~~~~~~~MW FLVLCLALSL GGTGAAPPIQ SRIVGGWECE QHSOPWQAAL   42
hPSA      ~~~~~~~MW VPVVFITLSV TWIGAAPLIL SRIVGGWECE KHSQPWQVLV   42
mNeur     MGRPPPCAIQ PWILLLLFMG AWAGLTRAQG SKILEGRECI PHSQPWQAAL   50
hTADG14   MGRPRPRAAK TWMFLLLGG  AWAGHSRAQE DKVLGGHECQ PHSQPWQAAL   50
hProM     ~~~~~MKK   LMVVISLIAA AWA.....EEQ NKLVHGGPCD KTSHPYQAAL   39 hHk2      YHFSTFQCGG ILVHRQWVLT AAHCISDNYQ LWLGRHNLFD DENTAQFVHV   92
hPSA      ASRGRAVCGG VLVHPQWVLT AAHCIRNKSV ILLGRHSLFH PEDTGQVFQV   92
mNeur     FQGERLICGG VLVGDRWVLT AAHCKKQKYS VRLGDHSLQS RDQPEQEIQV   100
hTADG14   FQGQLLCGG  VLVGGNWVLT AAHCKKPKYT VRLGDHSLQN KDGPEQEIPV   100
hProM     YTSGHLLCGG VLIHPLWVLT AAHCKKPNLQ VFLGKHNLRQ RESSQEQSSV   89
                                       Ÿ hHk2      SESFPHPGFN MSLLENHTRQ ADEDYSHDLM LLRLTEPADT ITDAVKVVEL   142
hPSA      SHSFPHPLYD MSLLKNRFLR PGDDSSHDLM LLRLSEPAE. LTDAVKVMDL   141
mNeur     AQSIQHPCYN NS........ NPEDHSHDIM LIRLQNSAN. LGDKVKPVQL   141
hTADG14   VQSIPHPCYN SS........ DVEDHNHDLM LLQLRDQAS. LGSKVKPISL   141
hProM     VRAVIHPDY. .......... DAASHDQDIM LLRLARPAK. LSELIQPLPL   127 hHk2      PTQEPEVGST CLASGWGSIE PENFSFPDDL QCVDLKILPN DECEKAHVQK   192
hPSA      PTQEPALGTT CYASGWGSIE PEEFLTPKKL QCVDLHVISN DVCAQVHPQK   191
mNeur     ANLCPKVGQK CIISGWGTVT SPQENFPNTL NCAEVKIYSQ NKCERAYPGK   191
hTADG14   ADHCTQPGQK CTVSGWGTVT SPRENFPDTL NCAEVKIFPQ KKCEDAYPGQ   191
hProM     ERDCSANTTS CHILGWGKTA D...GDFPDTI QCAYIHLVSR EECEHAYPGQ   175 hHk2      VTDFMLCVGH LEGGKDTCVG DSGGPLMCDG VLQGVTSWGY VPCGTPNKPS   242
hPSA      VTKFMLCAGR WTGGKSTCSG DSGGPLVCNG VLQGITSWGS EPCALPERPS   241
mNeur     ITEGMVCAGS SN.GADTCQG DSGGPLVCDG MLQGITSWGS DPCGKPEKPG   240
hTADG14   ITDGMVCAGS SK.GADTCQG DSGGPLVCDG ALQGITSWGS DPCGRSDKPG   240
hProM     ITQNMLCAGD EKYGKDSCQG DSGGPLVCGD HLRGLVSWGN IPCGSKEKPG   225 hHk2      VAVRVLSYVK WIEDTIAENS  SEQ ID NO: 9    262
hPSA      LYTKVVHYRK WIKDTIVANP  SEQ ID NO: 10   261
mNeur     VYTKICRYTT WIKKTMDNRD  SEQ ID NO: 8    260
hTADG14   VYTNICRYLD WIKKIIGSKG  SEQ ID NO: 7    260
hProM     VYTNVCRYTN WIQKTIQAK-  SEQ ID NO: 11   244
```

FIG. 3B

```
201        PRIMER
Prom    WVLTAAHC KK   PNLQV....F   LGKHNLRQRE   SSQEQSSVVR   AVIHPDY....
Tadg14  WVVTAAHC KK   PKYTV....R   LGDHSLQNKD   GPEQEIPVVQ   SIPHPCY....
Try1    WVVSAGHC YK   SRIQV....R   LGEHNIEVLE   GNEQFINAAK   IIRHPQY....
Scce    WVLTAAHC KM   NEYTV....H   LGSDTLGDRR   A..QRIKASK   SFRHPGY....
Heps    WVLTAAHC FP   ERNRVLSRWR   VFAGAVAQAS   PHGLGLGVQA   VVYHGGYLFF
                                                                    300
Prom    ...DAASHDQ   DIMLL RLARP   AKLSELIQPL   PLERDCSA..   NTTSCHILGW
Tadg14  NSSDVEDHNH   DLMLL QLRDQ   ASLGSKVKPI   SLADHCTQ..   PGQNCTVSGW
Try1    ...DRKTLNN   DIMLI KLSSR   AVINARVSTI   SLPTAPPA..   TGTKCLISGW
Scce    ST...QTHVN   DLMLV KLNSQ   ARLSSMVKKV   RLPSRCEP..   PGTTCTVSGW
Heps    RDPNSEENSN   DIALV HLSSP   LPLTEYIQPV   CLPAAGQALV   DGKICTVTGW
                                                                    350
Prom    GKTAD..GDF   PDTIQCAYIH   LVSREECEHA   ..TPGQITQN   MLCAGDEKYG
Tadg14  GTVTSPRENF   PDTLNCAEVK   IFPQKKCEDA   ..YPGQITDG   MVCAGSSK.G
Try1    GNTASSGADY   PDELQCLDAP   VLSQAKCEAS   ..YPGKITSN   MFCVGFLEGG
Scce    GTTTSPDVTF   PSDLMCVDVK   LISPQDCTKV   ..YKDLLENS   MLCAGIPDSK
Heps    GNTQYYGQQ.   AGVLQEARVP   IISNDVCNGA   DFYGNQIKPK   MFCAGYPEGG 351
Prom    KDSCQ GDSGG     SEQ ID No. 1
Tadg14  ADTCQ GDSGG     SEQ ID No. 2
Try1    KDSCQ GDSGG     SEQ ID No. 3
Scce    KNACN GDSGG     SEQ ID No. 4
Heps    IDACQ GDSGG     SEQ ID No. 5
              PRIMER
```

FIG. 4

```
Tadg 14                                               MGRPRPRAAK TWMFLLLLGG AWA.......  ..........  ..........
Tadg 14 V                                             MGRPRPRAAK TWMFLLLLGG AWAACGSLDL LTKLYAENLP CVHLNPQWPS Tadg 14   ..........  ..........  ........GH SRAQEDKVLG GHECQPHSQP WQAALFQGQQ
Tadg 14 V QPSHCPRGWR SNPLPPAAGH SRAQEDKVLG GHECQPHSQP WQAALFQGQQ Tadg 14   LLCGGVLVGG NWVLTAAHCK KPKYTVRLGD HSLQNKDGPE QEIPVVQSIP
Tadg 14 V LLCGGVLVGG NWVLTAAHCK KPKYTVRLGD HSLQNKDGPE QEIPVVQSIP Tadg 14   HPCYNSSDVE DHNHDLMLLQ LRDQASLGSK VKPISLADHC TQPGQKCTVS
Tadg 14 V HPCYNSSDVE DHNHDLMLLQ LRDQASLGSK VKPISLADHC TQPGQKCTVS Tadg 14   GWGTVTSPRE NFPDTLNCAE VKIFPQKKCE DAYPGQITDG MVCAGSSKGA
Tadg 14 V GWGTVTSPRE NFPDTLNCAE VKIFPQKKCE DAYPGQITDG MVCAGSSKGA Tadg 14   DTCQGDSGGP LVCDGALQGI TSWGSDPCGR SDKPGVYTNI CRYLDWIKKI
Tadg 14 V DTCQGDSGGP LVCDGALQGI TSWGSDPCGR SDKPGVYTNI CRYLDWIKKI Tadg 14   IGSKG  (SEQ ID NO. 7)
Tadg 14 V IGSKG  (SEQ ID NO. 75)
```

FIG. 11

EXTRACELLULAR SERINE PROTEASE

CROSS-REFERENCE TO RELATED APPLICATIONS

This patent application is a divisional of and claims benefit of priority under 35 U.S.C. §120 of U.S. Ser. No. 12/802,335, filed Jun. 4, 2010, now U.S. Pat. No. 8,216,794, which is a divisional under 35 U.S.C. §120 of U.S. Ser. No. 10/652,846, filed Aug. 29, 2003, now U.S. Pat. No. 7,732,163, which is a continuation-in-part under 35 U.S.C. §120 of U.S. Ser. No. 09/796,294, filed Feb. 28, 2001, now U.S. Pat. No. 7,157,084, which is a continuation-in-part under 35 U.S.C. 120 of U.S. Ser. No. 09/618,259, filed Jul. 18, 2000, now U.S. Pat. No. 6,642,013, which is a continuation-in-part under 35 U.S.C. §120 of U.S. Ser. No. 09/137,944, filed Aug. 21, 1998, now U.S. Pat. No. 7,067,250, which is a continuation-in-part under 35 U.S.C. §120 of U.S. Ser. No. 08/915,659, filed Aug. 21, 1997, now U.S. Pat. No. 7,014,993, the entirety of all of which hereby are incorporated reference.

BACKGROUND OF THE INVENTION

1. Field of the Invention

The present invention relates generally to the fields of cellular biology and the diagnosis of neoplastic disease. More specifically, the present invention relates to a novel extracellular serine protease termed Tumor Antigen Derived Gene-14 (TADG-14).

2. Description of the Related Art

Serine proteases comprise a family of protein degrading enzymes that serve a host of biological functions including activation of blood coagulation cascades, activation of growth and angiogenic factors and degradation of extracellular matrix components (1-4). In recent years, aberrant expression of serine proteases, such as plasminogen activator have been shown to correlate positively with the invasiveness and metastatic potential of tumor cells (3, 5-6). Presumably, this occurs by increasing the ability of the tumors to degrade extracellular matrix components either directly or indirectly through the proteolytic activation of other zymogenic proteases. More significantly, the serine protease known as the prostate specific antigen (PSA) has been used successfully as a tumor marker for the early diagnosis of prostate cancer due to its abnormal prevalence in the peripheral blood of these patients (7). Serine proteases play important roles in the cascade of events involved in the malignant process, and at least for prostate cancer, they provide sufficient signal to allow detection of early disease.

The prior art is deficient in the lack of effective means of screening to identify proteases overexpressed in carcinoma. The present invention fulfills this longstanding need and desire in the art.

SUMMARY OF THE INVENTION

The present invention discloses a 1343 base pairs long TADG-14 cDNA (SEQ ID No: 6) which encodes a 260 amino acid protein (SEQ ID No: 7) overexpressed in carcinoma. The availability of the TADG-14 gene opens the way for a number of studies that can lead to various applications.

In one embodiment of the present invention, there is provided a DNA encoding a TADG-14 protein having the amino acid sequence of SEQ ID NO. 7, a vector capable of expressing the DNA of the present invention, as well as host cell transfected with the vector that express the TADG-14 protein. Additionally embodied is a vector in which the TADG-14 DNA is positioned in reverse orientation relative to the regulatory elements such that a TADG-14 antisense DNA is produced.

In another embodiment of the present invention, there is provided a DNA encoding a TADG-14 variant protein having the amino acid sequence of SEQ ID NO. 75 or fragments thereof, a vector capable of expressing said DNA, as well as host cell transfected with the vector that express the TADG-14 variant protein. The TADG-14 protein variant has a potential role for detecting and targeting of ovarian carcinomas.

The present invention also provides an isolated and purified TADG-14 protein (SEQ ID No: 7) and an isolated and purified TADG-14 variant protein (SEQ ID No: 75) or fragments of either protein. The present invention also provides antibodies or antibody fragments specific for the TADG-14 protein or the TADG-14 variant protein.

In another embodiment of the present invention, there are provided methods of using oligonucleotide probe, antibody or antibody fragments to detect TADG-14 mRNA, TADG-14 variant mRNA, TADG-14 protein, or TADG-14 variant protein in a biological sample. Generally, the sample is a biological sample from blood, interstitial fluid, ascites fluid, tumor tissue biopsy or circulating tumor cells. Preferably, the biological sample is from an individual; and typically, the individual is suspected of having cancer.

The present invention also provides kits for detecting TADG-14 mRNA, TADG-14 variant mRNA, TADG-14 protein, or TADG-14 variant protein. The kits comprises oligonucleotide probe, antibody or antibody fragments specific for TADG-14 or TADG-14 variant. The kits can further comprise a label for detecting the probe or antibody.

In yet another embodiment of the present invention, there is provided methods of inhibiting expression of TADG-14 in a cell with TADG-14 antisense DNA or TADG-14-specific antibody. Generally, the inhibition of TADG-14 expression is for treating cancer.

In another embodiment of the present invention, there is provided a method of targeted therapy to an individual, comprising the step of: (a) administering a compound containing a targeting moiety and a therapeutic moiety to an individual, wherein the targeting moiety is specific for TADG-14.

In another embodiment of the present invention, there are provided methods of diagnosing cancer in an individual through the detection of TADG-14 or TADG-14 variant at the protein or DNA level.

In yet another embodiment of the present invention, there is provided a method of vaccinating an individual against TADG-14 protein, comprising the step of (a) inoculating an individual with a TADG-14 protein or fragment thereof which lacks TADG-14 protease activity. Typically, inoculation with the TADG-14 protein or fragment thereof elicits an immune response in the individual, thereby vaccinating the individual against TADG-14. Generally, the individual has cancer, is suspected of having cancer or is at risk of getting cancer. Preferably, the TADG-14 fragment is a 9-residue fragment up to a 20-residue fragment, and more preferably, the 9-residue fragment is SEQ ID Nos. 17, 18, 41, 42, 47, 48, 53, 56, or 64.

In another embodiment of the present invention, there is provided a method of producing activated immune cells directed toward TADG-14, comprising the steps of exposing immune cells to a TADG-14 protein or fragment thereof which lacks TADG-14 protease activity. Usually, exposure to the TADG-14 protein or fragment thereof activates the immune cells, thereby producing activated immune cells directed toward TADG-14. Generally, the immune cells are B cells, T cells or dendritic cells. Preferably, the dendritic cells are isolated from an individual prior to exposure to a TADG- 14 protein or fragment thereof, and then reintroduced into the individual subsequent to the exposure. Typically, the individual has cancer, is suspected of having cancer or is at risk of getting cancer. Preferably, the TADG-14 fragment is a 9-residue fragment up to a 20-residue fragment, and more preferably, the 9-residue fragment is SEQ ID Nos. 17, 18, 41, 42, 47, 48, 53, 56, or 64.

In another embodiment of the present invention, there is provided an immunogenic composition, comprising an immunogenic fragment of a TADG-14 protein and an appropriate adjuvant. Preferably, the TADG-14 fragment is a 9-residue fragment up to a 20-residue fragment, and more preferably, the 9-residue fragment is SEQ ID Nos. 17, 18, 41, 42, 47, 48, 53, 56, or 64.

In another embodiment of the present invention, there is provided an oligonucleotide having a sequence complementary to SEQ ID No. 6, as well as a composition comprising the oligonucleotide and a physiologically acceptable carrier. Additionally, there is provided a method of treating a neoplastic state in an individual in need of such treatment, comprising the step of (a) administering to the individual an effective dose of the above-described oligonucleotide.

Other and further aspects, features, and advantages of the present invention will be apparent from the following description of the presently preferred embodiments of the invention given for the purpose of disclosure.

BRIEF DESCRIPTION OF THE DRAWINGS

FIGS. 2A-2D show the Northern blot analysis of TADG-14. FIG. 2A shows messenger RNA isolated from the tissues of interest was subjected to Northern hybridization using a random labeled 230 bp TADG-14 specific RT-PCR product. The blot was stripped and probed for b-tubulin. FIGS. 2B, 2C, and 2D show multiple tissue Northern blots (Clontech) probed with the same TADG-14 and b-tubulin specific RT-PCR products. TADG-14 mRNA was detected as a 1.4-kb transcript in tumors but not in any normal tissue studied.

FIGS. 3A-3B shows the cDNA and deduced amino acid sequences of TADG-14 and comparison of predicted TADG-14 sequence with known proteases. FIG. 3A shows the cDNA sequence of TADG-14 with its deduced 260 amino acid sequence represented by the one-letter code for each residue. Within the cDNA, the underlined bold italics and underlined bold portions represent the Kozak's consensus sequence for initiation of translation and the polyadenylation signal, respectively. The TADG-14 protein sequence contains a secretion signal sequence near its amino terminus. The stop codon is represented by the (*) symbol. FIG. 3B shows the amino acid sequence of TADG-14 compared to human glandular kallikrein (hHk2, accession #P06870), human PSA (hPSA, accession # P07288), mouse neuropsin (mNeur, accession #D30785) and human Protease M (hProM, accession #U62801) using the GCG PILEUP program (REF). The positions of the residues of the catalytic triad are marked Y.

FIG. 4 shows a comparison of the amino acid sequence of TADG-14's catalytic domains.

FIG. 5A shows the typical results of a TADG-14 quantitative PCR experiment. The reaction products were electrophoresed through a 2% agarose TAE gel and stained with ethidium bromide. In this figure, the 454-bp band represents the b-tubulin product and the 230-bp band represents the TADG-14 product. The radiolabeled PCR products were quantitated. FIG. 5B shows the overexpression of TADG-14. As determined by the student's t test, TADG-14 mRNA expression levels were significantly elevated in LMP tumors (*, $P=0.05$) and carcinomas ($P<0.0001$) compared to levels found in normal ovary. Individual cases are represented in a scatter plot. This is indicative of heterogeneity of TADG-14 expression among these tumor samples.

FIG. 11 shows amino acid sequence comparison of TADG-14 and TADG-14 variant.

DETAILED DESCRIPTION OF THE INVENTION

All serine proteases contain conserved histidine, aspartate and serine residues that are necessary for enzymatic activity. To identify the expressed serine proteases in carcinoma, degenerate oligodeoxynucleotide primers designed to the conserved amino acid sequences surrounding the invariant His and Ser residues of the catalytic triad (8) were used in PCR reactions with cDNA from either normal ovarian tissue or ovarian carcinoma as the template. PCR products of the appropriate size were subcloned into T-vector and sequenced. Previously, this strategy has proved successful in identifying the serine proteases hepsin and stratum corneum chymotryptic enzyme (SCCE) which have been shown to be expressed at abnormally high levels in ovarian carcinoma (9, 10).

Homology searches revealed that one of the subclones obtained from ovarian carcinoma represented a novel 406 base pair (bp) sequence that has significant sequence similarity to other known proteases including mouse neuropsin, human glandular kallikrein and human PSA. The complete cDNA for this novel sequence was cloned and found to encode a trypsin like serine protease, named TADG-14. The TADG-14 cDNA is 1343 base pairs long (SEQ ID No: 6) and encoding for a 260 amino acid protein (SEQ ID No: 7).

The availability of the TADG-14 gene opens the way for a number of studies that can lead to various applications. More importantly, the TADG-14 transcript was found to be highly expressed in a majority of ovarian tumors but not expressed by normal ovarian tissue. High level expression of TADG-14 appears to be restricted to tumors, and this protease appears to be secreted in a manner that would suggest a possible role in invasion and metastasis. Moreover, due to the extracellular nature of this enzyme, it may be possible to exploit its expression as a diagnostic tool for ovarian cancer.

Figure 10:
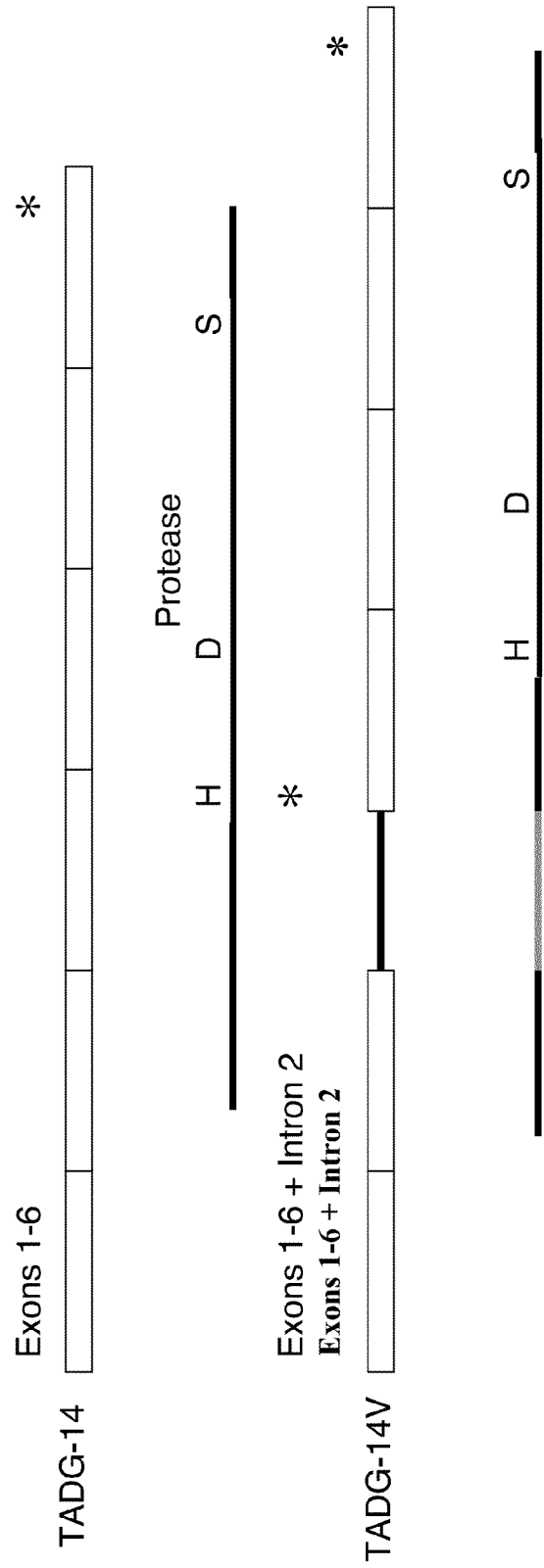
FIG. 10 presents a diagram of transcript and open reading frame of TADG-14 and TADG-14 variant including intron 2.

The present invention also discloses a TADG-14 variant that includes intron sequence between exon 2 and exon 3. This TADG-14 variant could be translated into an extended amino acid sequence which presumably would still have protease activity (FIGS. 10-11). The addition of the intron sequence and the subsequent translation into additional amino acid sequence provides an opportunity to add unique specificity for diagnostic detection and/or targeting of tumor therapy. This variant was expressed in 5 out of 6 ovarian carcinomas examined. Normal ovary cells did not express this TADG-14 variant.

In accordance with the present invention there may be employed conventional molecular biology, microbiology, and recombinant DNA techniques within the skill of the art. Such techniques are explained fully in the literature. See e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The amino acids described herein are preferred to be in the "L" isomeric form. However, residues in the "D" isomeric form can be substituted for any L-amino acid residue, as long as the desired functional property is retained by the polypeptide. It should be noted that all amino-acid residue sequences are represented herein by formulae whose left and right orientation is in the conventional direction of amino-terminus to carboxy-terminus.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

As used herein, the term "host" is meant to include not only prokaryotes but also eukaryotes such as yeast, plant and animal cells. A recombinant DNA molecule or gene which encodes a human TADG-14 protein of the present invention can be used to transform a host using any of the techniques commonly known to those of ordinary skill in the art. Especially preferred is the use of a vector containing coding sequences for the gene which encodes a human TADG-14 protein of the present invention for purposes of prokaryote transformation.

Prokaryotic hosts may include *E. coli, S. tymphimurium, Serratia marcescens* and *Bacillus subtilis*. Eukaryotic hosts include yeasts such as *Pichia pastoris*, mammalian cells and insect cells.

The invention includes a substantially pure DNA encoding a TADG-14 protein, containing a sequence of at least 15 consecutive nucleotides (preferably 20, more preferably 30, even more preferably 50, and most preferably all) of the region from nucleotides 1 to 1343 of the nucleotides listed in SEQ ID NO: 6. The protein encoded by the DNA of this invention may share at least 80% sequence identity (preferably 85%, more preferably 90%, and most preferably 95%) with the amino acids listed in SEQ ID NO: 7. More preferably, the DNA includes the coding sequence of the nucleotides of SEQ ID NO: 6, or a degenerate variant of such a sequence.

"Substantially pure DNA" is DNA that is part of a milieu in which the DNA does not naturally occurs. The DNA can be obtained by virtue of separation (partial or total purification) of some or all of the molecules of that milieu, or by virtue of alteration of sequences that flank the claimed DNA. The term therefore includes, for example, a recombinant DNA which is incorporated into a vector, an autonomously replicating plasmid or virus, the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in SEQ ID NO: 6 which encodes an alternative splice variant of TADG-14.

The present invention encompasses DNA that have at least about 70% sequence identity to the coding sequence of the nucleotides listed in SEQ ID NO: 6, preferably at least 75% (e.g. at least 80%); and most preferably at least 90%. The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

The invention also includes DNA that hybridizes at high stringency to a probe containing at least 15 consecutive nucleotides of SEQ ID NO: 6. The probe to which the DNA of the invention hybridizes preferably consists of a sequence of at least 20 consecutive nucleotides, more preferably 40 nucleotides, even more preferably 50 nucleotides, and most preferably 100 nucleotides or more (up to 100%) of the coding sequence of the nucleotides listed in SEQ ID NO: 6 or the complement thereof. Such a probe is useful for detecting expression of TADG-14 in a cell by a method including the steps of (a) contacting mRNA obtained from the cell with the labeled hybridization probe; and (b) detecting hybridization of the probe with the mRNA.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

The present invention further comprises a vector comprising a DNA sequence which encodes a human TADG-14 protein or a human TADG-14 variant protein. The vector comprises in operable linkage: a) an origin of replication; b) a promoter; and c) a DNA sequence coding for said protein. Preferably, the vector of the present invention contains a portion of the DNA sequence shown in SEQ ID No: 6 or encode a TADG-14 variant having the amino acid sequence of SEQ ID NO. 75.

A "vector" may be defined as a replicable nucleic acid construct, e.g., a plasmid or viral nucleic acid. Vectors may be used to amplify and/or express nucleic acid encoding TADG-14 protein. An "expression vector" is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

Further included in this invention are substantially pure TADG-14 protein or TADG-14 variant protein which are encoded at least in part by portions of SEQ ID NO. 7 and SEQ ID NO. 75 respectively. The protein products include alternative mRNA splicing or alternative protein processing events, or in which a section of TADG-14 sequence has been deleted. The fragment, or the intact TADG-14 polypeptide, may be covalently linked to another polypeptide, e.g. which acts as a label, a ligand or a means to increase antigenicity.

By a "substantially pure protein" is meant a protein which has been separated from at least some of those components which naturally accompany it. Typically, the protein is substantially pure when it is at least 60% by weight free from the proteins and other naturally-occurring organic molecules with which it is naturally associated in vivo. Preferably, the purity of the preparation is at least 75%, more preferably at least 90%, and most preferably at least 99%, by weight. A substantially pure TADG-14 protein or TADG-14 variant may be obtained, for example, by extraction from a natural source; by expression of a recombinant nucleic acid encoding a TADG-14 or TADG-14 variant polypeptide; or by chemically synthesizing the protein. Purity can be measured by any appropriate method, e.g., column chromatography such as immunoaffinity chromatography using an antibody specific for TADG-14 or TADG-14 variant, polyacrylamide gel electrophoresis, or HPLC analysis. A protein which is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

In addition to substantially full-length proteins, the invention also includes fragments (e.g., antigenic fragments) of the TADG-14 or TADG-14 variant protein. As used herein, "fragment," as applied to a polypeptide, will ordinarily be at least 10 residues, more typically at least 20 residues, and preferably at least 30 (e.g., 50) residues in length, but less than the entire, intact sequence. Fragments of the TADG-14 or TADG-14 variant protein can be generated by methods known to those skilled in the art, e.g., by enzymatic digestion of naturally occurring or recombinant TADG-14 or TADG-14 variant protein, by recombinant DNA techniques using an expression vector that encodes a defined fragment of TADG-14 or TADG-14 variant, or by chemical synthesis. The ability of a candidate fragment to exhibit a characteristic of TADG-14 (e.g., binding to an antibody specific for TADG-14) can be assessed by methods described herein. Purified TADG-14 or antigenic fragments of TADG-14 can be used to generate new antibodies or to test existing antibodies (e.g., as positive controls in a diagnostic assay) by employing standard protocols known to those skilled in the art.

Included in this invention are polyclonal or monoclonal antibodies specific for TADG-14 or TADG-14 variant. Standard protocols for monoclonal and polyclonal antibody production known to those skilled in this art are employed. The monoclonal antibodies generated by this procedure can be screened for the ability to identify recombinant TADG-14 cDNA clones, and to distinguish them from known cDNA clones.

The invention encompasses not only an intact polyclonal or monoclonal antibody, but also an immunologically-active antibody fragment that recognizes TADG-14 or TADG-14 variant, e.g., a Fab or (Fab)$_2$ fragment; an engineered single chain Fv molecule; or a chimeric antibody in which the antigen binding sites are derived from murine antibody while the remaining portions of the antibody are of human origin.

In one embodiment, the antibody, or a fragment thereof, may be linked to a toxin or to a detectable label, e.g. a radioactive label, non-radioactive isotopic label, fluorescent label, chemiluminescent label, paramagnetic label, enzyme label, or colorimetric label. Examples of suitable toxins include diphtheria toxin, Pseudomonas exotoxin A, ricin, and cholera toxin. Examples of suitable enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc. Examples of suitable radioisotopic labels include $^3H$, $^{125}I$, $^{131}I$, $^{32}P$, $^{35}S$, $^{14}C$, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) *JACC* 14, 472-480; Shreve et al., (1986) *Magn. Reson. Med.* 3, 336-340; Wolf, G. L., (1984) *Physiol. Chem. Phys. Med. NMR* 16, 93-95; Wesbey et al., (1984) *Physiol. Chem. Phys. Med. NMR* 16, 145-155; Runge et al., (1984) *Invest. Radiol.* 19, 408-415. Examples of suitable fluorescent labels include a fluorescein label, an isothiocyalate label, a rhodamine label, a phycoerythrin label, a phycocyanin label, an allophycocyanin label, an ophthaldehyde label, a fluorescamine label, etc. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy et al., (1976) *Clin. Chim. Acta* 70, 1-31; and Schurs et al., (1977) *Clin. Chim. Acta* 81, 1-40. Coupling techniques mentioned in the latter are the glutaraldehyde method, the periodate method, the dimaleimide method, the m-maleimidobenzyl-N-hydroxysuccinimide ester method. All of these methods are incorporated by reference herein.

As described herein, the invention provides a number of diagnostic advantages and uses. For example, the TADG-14 or TADG-14 variant protein is useful in diagnosing cancer in different tissues since this protein is absent in highly proliferating cells. Antibodies (or antigen-binding fragments thereof) which bind to an epitope specific for TADG-14 or TADG-14 variant are useful in a method of detecting TADG-14 protein in a biological sample for diagnosis of cancerous or neoplastic transformation. This method includes the steps of obtaining a biological sample (e.g., cells, blood, plasma, tissue, etc.) from a patient suspected of having cancer, contacting the sample with a labelled antibody (e.g., radioactively tagged antibody) specific for TADG-14 or TADG-14 variant, and detecting the TADG-14 protein using standard immunoassay techniques such as an ELISA. Antibody binding to the biological sample indicates that the sample contains a component which specifically binds to an epitope within TADG-14.

Likewise, a standard Northern blot assay can be used to ascertain the relative amounts of TADG-14 or TADG-14 variant mRNA in a cell or tissue obtained from a patient suspected of having cancer. Northern assay usually uses a hybridization probe, e.g. a full-length, single stranded radiolabelled TADG-14 cDNA probe having a sequence complementary to SEQ ID NO: 6, or a fragment of that DNA sequence at least 20 (preferably at least 30, more preferably at least 50, and most preferably at least 100) consecutive nucleotides in length. The DNA hybridization probe can be labelled by any of the many different methods known to those skilled in this art.

In another embodiment of the present invention, there is provided a method of inhibiting expression of TADG-14 in a cell, comprising the step of: (a) introducing a vector into a cell, whereupon expression of the vector produces TADG-14 antisense DNA which hybridizes to endogenous TADG-14 mRNA and inhibits expression of TADG-14 in the cell.

Further embodied by the present invention, there is provided a method of inhibiting a TADG-14 protein in a cell, comprising the step of: (a) introducing an antibody specific for TADG-14 protein or a fragment thereof into a cell, whereupon binding of the antibody to the TADG-14 protein inhibits the TADG-14 protein in said cell.

The present invention is also directed toward a method of targeted therapy to an individual, comprising the step of: (a) administering a compound having a targeting moiety and a therapeutic moiety to an individual, wherein the targeting moiety is specific for TADG-14. Representative targeting moieties are an antibody specific for TADG-14 and a ligand or ligand binding domain that binds TADG-14. Likewise, a representative therapeutic moiety is a radioisotope, a toxin, a chemotherapeutic agent and immune stimulants. Typically, the above-described method is useful when the individual suffers from ovarian cancer, breast cancer or cancers of the prostate, lung, colon and cervix.

The present invention also provides methods of diagnosing cancer in an individual, comprising the steps of: (a) obtaining a biological sample from an individual; and (b) detecting TADG-14 or TADG-14 variant in the sample. Generally, the presence of TADG-14 or TADG-14 variant in the sample is indicative of the presence of carcinoma in the individual. Generally, the biological sample is blood, ascites fluid, interstitial fluid, tumor tissue biopsy or tumor cells. Typical means of detecting TADG-14 or TADG-14 variant are by Northern blot, Western blot, PCR, dot blot, ELISA, radioimmunoassay, DNA chips or tumor cell labeling. This method may be useful in diagnosing cancers such as ovarian, breast, prostate and colon cancers.

In still yet another embodiment of the present invention, there is provided a method of vaccinating an individual against TADG-14 protein, comprising the step of (a) inoculating an individual with a TADG-14 protein or fragment thereof which lacks TADG-14 protease activity. Typically, inoculation with the TADG-14 protein or fragment thereof elicits an immune response in the individual, thereby vaccinating the individual against TADG-14. Generally, the individual has cancer, is suspected of having cancer or is at risk of getting cancer. Preferably, the TADG-14 fragment is a 9-residue fragment up to a 20-residue fragment, and more preferably, the 9-residue fragment is SEQ ID Nos. 17, 18, 41, 42, 47, 48, 53, 56, or 64.

In another embodiment of the present invention, there is provided a method of producing activated immune cells directed toward TADG-14, comprising the steps of exposing immune cells to a TADG-14 protein or fragment thereof which lacks TADG-14 protease activity. Usually, exposure to the TADG-14 protein or fragment thereof activates the immune cells, thereby producing activated immune cells directed toward TADG-14. Generally, the immune cells are B cells, T cells or dendritic cells. Preferably, the dendritic cells are isolated from an individual prior to exposure to a TADG-14 protein or fragment thereof, and then reintroduced into the individual subsequent to the exposure. Typically, the individual has cancer, is suspected of having cancer or is at risk of getting cancer. Preferably, the TADG-14 fragment is a 9-residue fragment up to a 20-residue fragment, and more preferably, the 9-residue fragment is SEQ ID Nos. 17, 18, 41, 42, 47, 48, 53, 56, or 64.

In another embodiment of the present invention, there is provided an immunogenic composition, comprising an immunogenic fragment of a TADG-14 protein and an appropriate adjuvant. Preferably, the TADG-14 fragment is a 9-residue fragment up to a 20-residue fragment, and more preferably, the 9-residue fragment is SEQ ID Nos. 17, 18, 41, 42, 47, 48, 53, 56, or 64.

In another embodiment of the present invention, there is provided an oligonucleotide having a sequence complementary to SEQ ID No. 6, as well as a composition comprising the oligonucleotide and a physiologically acceptable carrier. Additionally, there is provided a method of treating a neoplastic state in an individual in need of such treatment, comprising the step of (a) administering to the individual an effective dose of the above-described oligonucleotide.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Cloning and Characterization of TADG-14
Tissue Collection and Storage

Upon patient hysterectomy, bilateral salpingo-oophorectomy, or surgical removal of neoplastic tissue, the specimen was retrieved and placed it on ice. The specimen was then taken to the resident pathologist for isolation and identification of specific tissue samples. Finally, the sample was frozen in liquid nitrogen, logged into the laboratory record and stored at −80° C. Additional specimens were frequently obtained from the Cooperative Human Tissue Network (CHTN). These samples were prepared by the Cooperative Human Tissue Network and shipped on dry ice. Upon arrival, these specimens were logged into the laboratory record and stored at −80° C.

mRNA Isolation and cDNA Synthesis

Messenger RNA (mRNA) isolation was performed according to the manufacturer's instructions using the Mini RiboSep™ Ultra mRNA isolation kit purchased from Becton Dickinson. This was an oligo(dT) chromatography based system of mRNA isolation. The amount of mRNA recovered was quantitated by UV spectrophotometry.

First strand complementary DNA (cDNA) was synthesized using 5.0 ug of mRNA and either random hexamer or oligo (dT) primers according to the manufacturer's protocol utilizing a first strand synthesis kit obtained from Clontech. The purity of the cDNA was evaluated by PCR using primers specific for the p53 gene. These primers span an intron such that pure cDNA can be distinguished from cDNA that is contaminated with genomic DNA.

PCR Reactions

Reactions with degenerate primers and quantitative PCR reactions were carried out as previously described (10,11). The sequences of the TADG-14 specific primers that produce the 230 bp product were as follows: 5'-ACAGTACGCCTGG-GAGACCA-3' (SEQ ID No. 12) and 5'-CTGAGACGGTG-CAATTCTGG-3' (SEQ ID No. 13).

T-Vector Ligation and Transformations

The purified PCR products were ligated into the Promega T-vector plasmid and the ligation products were used to transform JM109 competent cells according to the manufacturer's instructions. Positive colonies were cultured for amplification, the plasmid DNA isolated by means of the Wizard™ Minipreps DNA purification system, and the plasmids were digested with ApaI and SacI restriction enzymes to determine the size of the insert. Plasmids with inserts of the size(s) visualized by the previously described PCR product gel electrophoresis were sequenced.

DNA Sequencing

Utilizing a plasmid specific primer near the cloning site, sequencing reactions were carried out using PRISM™ Ready Reaction Dye Deoxy™ terminators (Applied Biosystems) according to the manufacturer's instructions. Residual dye terminators were removed from the completed sequencing reaction using a Centri-sep™ spin column (Princeton Separation). An Applied Biosystems Model 373A DNA Sequencing System was used for sequence analysis. Sequences were compared to GenEMBL databases using the FASTA program (Wisconsin Package Version 9.1, Genetics Computer Group (GCG), Madison, Wis.) Multiple sequence alignments were generated with the Bestfit and Pileup programs available through Genetics Computer Group.

Northern Blot Analysis mRNAs (approximately 5 mg) were size separated by electrophoresis through a 6.3% formaldehyde, 1.2% agarose gel in 0.02 M MOPS, 0.05 M sodium acetate (pH 7.0), and 0.001 M EDTA. The mRNAs were then blotted to Hybond-N (Amersham) by capillary action in 20×SSPE. The RNAs were fixed to the membrane by baking for 2 hours at 80° C. Additional multiple tissue northern (MTN) blots were purchased from CLONTECH Laboratories, Inc., including the Human multiple tissue northern blot (cat.#7760-1), the Human multiple tissue northern II blot (cat.#7759-1), the Human Fetal multiple tissue northern II blot (cat.#7756-1), and the Human Brain multiple tissue northern III blot (cat.#7750-1). The 230 bp TADG-14 specific PCR product was radiolabelled utilizing the Prime-a-Gene Labelling System available from Promega. The blots were probed and stripped according to the ExpressHyb Hybridization Solution protocol available from CLONTECH.

Antibody Production and Western Blot Analysis

Polyclonal antibodies were generated by immunization of white New Zealand rabbits with one of three poly-lysine linked multiple antigen peptides derived from the deduced amino acid sequence of TADG-14. These sequences are KYTVRLGDHSLQ (T14-1, SEQ ID No. 14), GHECQPHSQPWQ (T14-2, SEQ ID No. 15), and LDWIKKIIGSKG (T14-3, SEQ ID No. 16). For Western blot analysis, approximately 20 ug of MDA-MB-4355 and HeLa cell lysates were separated on a 15% SDS-PAGE gel and electroblotted to PVDF at 100V for 40 minutes at 4.degree.C. The blot was blocked overnight in Tris-buffered saline (TBS), pH 7.8 containing 0.2% non-fat milk. Primary antibody was added to the membrane at a dilution of 1:100 in 0.2% milk/TBS and incubated for 2 hours at room temperature. The blot was washed and incubated with a 1:3000 dilution of alkaline-phosphatase conjugated goat anti-rabbit IgG antibody (Bio-Rad) for one hour at room temperature. The blot was washed and incubated with a chemiluminescent substrate (Bio-Rad) before a 10-second exposure to X-ray film for visualization.

Immunohistochemistry

Immunohistochemical staining was performed using a Vectastain Elite ABC Kit (Vector). Formalin fixed and paraffin embedded specimens were routinely deparaffinized and processed using microwave heat treatment in 0.01 M sodium citrate buffer (pH 6.0). The specimens were incubated in methanol with 0.3% $H_2O_2$ for 30 minutes at room temperature and then incubated with normal goat serum for 30 minutes. The samples were incubated with anti-TADG-14 peptide derived polyclonal antibody for 1 hour at room temperature in a moisture chamber, followed by incubation with biotinylated anti-rabbit IgG for 30 minutes, and then incubated with ABC reagent (Vector) for 30 minutes. The final products were visualized using the AEC substrate system (DAKO) and sections were counter stained with hematoxylin before mounting. Negative controls were performed by using normal serum instead of the primary antibody.

Cloning Results

Figure 1:
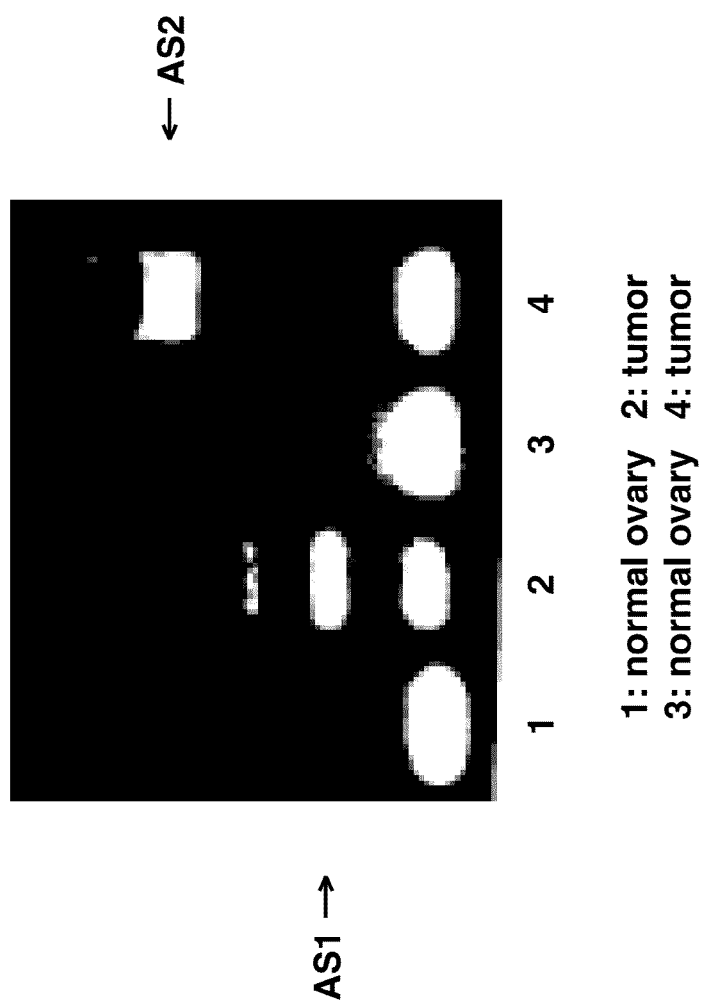
FIG. 1 shows a comparison of PCR products derived from normal and carcinoma cDNA as shown by staining in an agarose gel. Two distinct bands (lane 2) were present in the primer pair sense-His-antisense Asp (AS1) and multiple bands of about 500 base pairs are noted in the carcinoma lane for the sense-His antisense-Ser (AS2) primer pairs (lane 4).

The gene encoding the novel extracellular serine protease of the present invention was identified from a group of proteases overexpressed in carcinoma by subcloning and sequencing the appropriate PCR products. An example of such a PCR reaction is given in FIG. 1. Subcloning and sequencing of individual bands from such an amplification provided a basis for identifying the novel protease of the present invention.

Figure 2C:
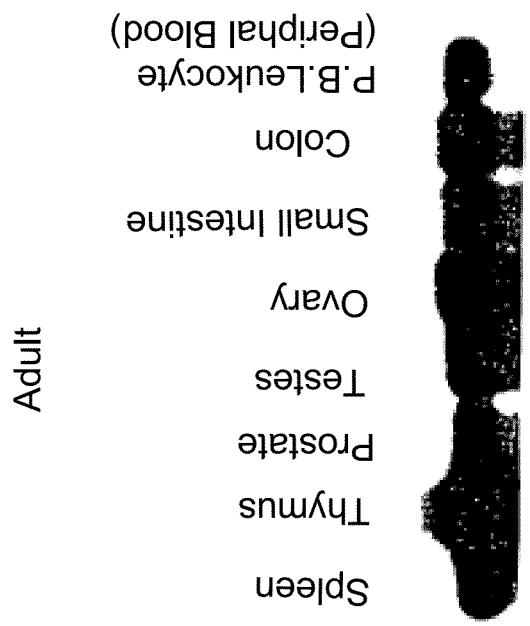
Figure 2B:
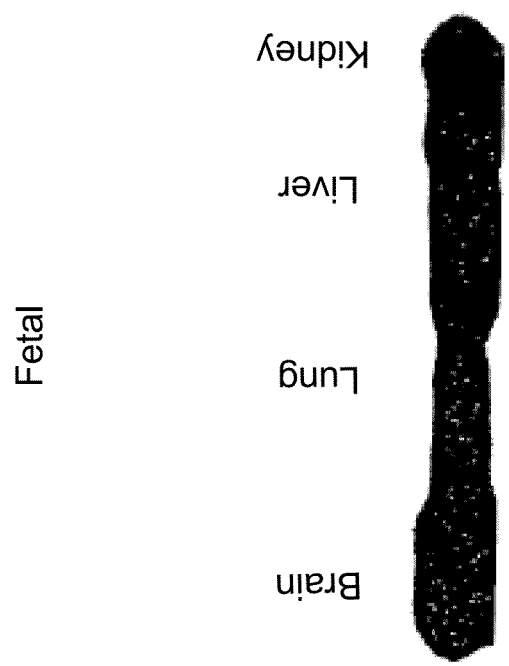

After confirming the 406 bp PCR product was unique and was appropriately conserved to fit into the serine protease family, this PCR product was used as a probe for Northern blot analysis to determine the transcript size and tissue specificity of its expression. It was found that the mRNA for this clone is approximately 1.4 kilobases (kb) (FIG. 2A), and that it is strongly expressed in ovarian carcinomas but not in normal ovary. More importantly, the transcript was found to be undetectable by Northern analysis in 28 normal human tissues studied (FIG. 2B, 2C, 2D and data not shown). In a more sensitive assay of 50 normal human tissues (Clontech), RNA dot blot analysis revealed that this clone was very weakly expressed in only three of these 50 tissues, kidney, lung and mammary gland (data not shown).

Using standard hybridization techniques, a cDNA library constructed from the mRNA isolated from the ascites cells of an ovarian cystadenocarcinoma patient was screened. Five clones were obtained, two of which overlapped and spanned 1343 nucleotides (FIG. 3A). The last two nucleotides prior to the poly (A) tail and the poly (A) tail itself were obtained from the EST database available at NCBI (accession #AA343629). Subsequent Northern blot analyses with probes derived from sequences near the 5' or 3' end of this cDNA were consistent with previous results suggesting that the obtained clones were produced by the same gene (data not shown). This cDNA includes a Kozak's consensus sequence for the initiation of translation, and a polyadenylation signal.

The mRNA provides an open reading frame of 260 amino acids, which contains the necessary residues ($His^{73}$, $Asp^{120}$, $Ser^{212}$) in the appropriate context to classify this protein as a trypsin-like serine protease (1). Near its amino-terminus, the predicted protein contains a stretch of hydrophobic amino acids that probably serve as a secretion signal sequence. In addition, residues 110 to 112 encode a potential site for glycosylation that is common to serine proteases of the kallikrein subfamily such as PSA. This enzyme was named TADG-14, and the sequence was submitted to GenBank and assigned the accession #AF055982.

Comparison of the deduced TADG-14 amino acid sequence with sequences of known proteases revealed that it possesses significant similarity with human glandular kallikrein (hHk2), PSA, Protease M and mouse neuropsin (11-14). The sequence determined for the catalytic domain of TADG-14 is presented in FIG. 4 and is consistent with other serine proteases and specifically contains conserved amino acids appropriate for the catalytic domain of the serine protease family. At the amino acid level TADG-14 is 48% identical to Protease M, 46% identical to hHk2, and 43% identical to PSA (FIG. 3B). More interestingly, the mouse protease neuropsin and TADG-14 share 72% amino acid identity. In addition to the similarity of the protein sequences, neuropsin and TADG-14 mRNAs are of similar size (1.4 kb) and structure with approximately the same amounts of 5' and 3' untranslated regions suggesting the possibility of orthology. Neuropsin was originally identified as being expressed in mouse hippocampus and shown to be differentially expressed under stimulation (14). However, TADG-14 mRNA was undetectable in human whole brain by Northern blot. Further, Northern blot analysis for TADG-14 in eight separate parts of human brain including amygdala, caudate nucleus, corpus callosum, hippocampus, whole brain, substantia nigra, subthalamic nucleus and thalmus, also turned out to be negative. Recently, a human cDNA encoding neuropsin has been submitted to the GenBank database (accession # AB009849). Although this clone represents a different transcript from TADG-14, it encodes a protein that is identical to TADG-14 (15). Therefore, it seems logical that TADG-14 and neuropsin may arise as alternative splicing products from the same gene.

Figure 5A:
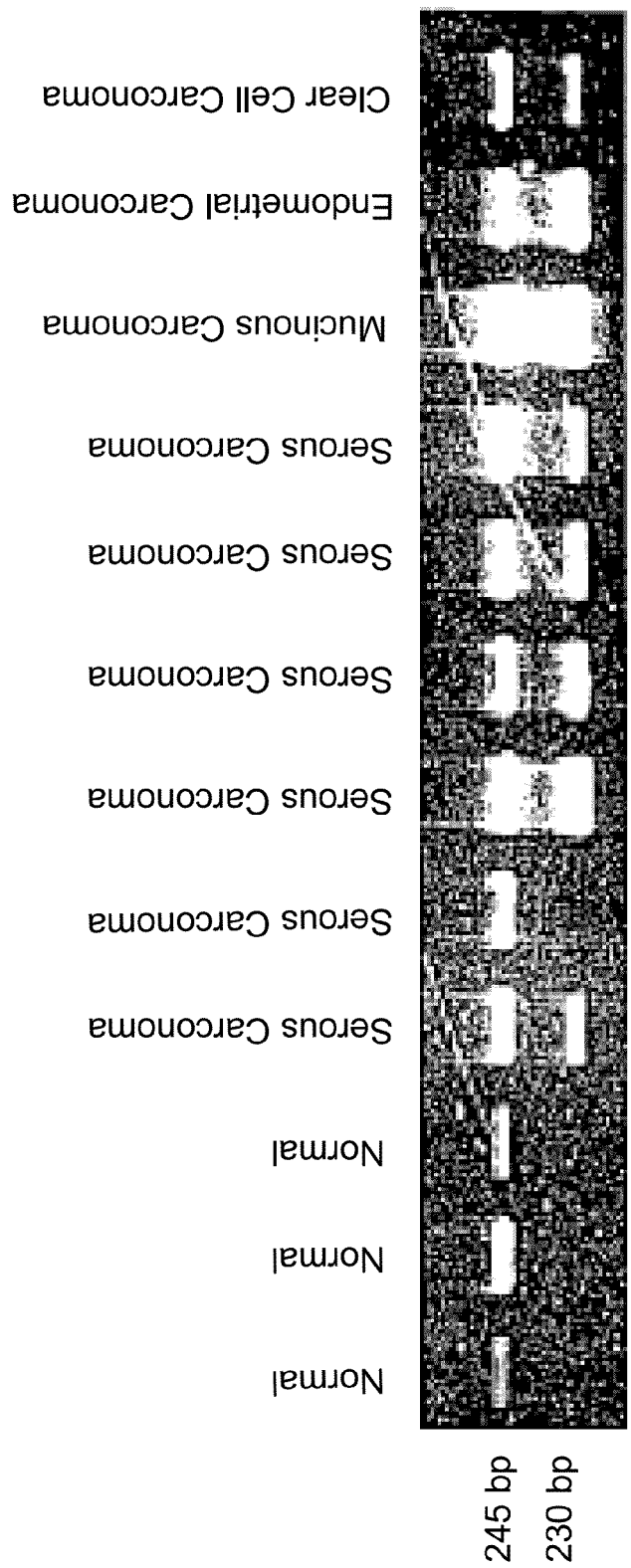
FIGS. 5A-5B show the TADG-14 quantitative PCR.

To characterize the extent and frequency of expression of the TADG-14 gene in ovarian tumors, semi-quantitative PCR was performed with cDNA derived from normal ovary, ovarian carcinoma or low malignant potential (LMP) tumors as template. This technique has been previously authenticated and verified by Northern blot, Western blot and immunohistochemistry (9, 16). PCR primers that amplify a TADG-14 specific 230 bp product were synthesized and used simultaneously in reactions with primers that produce a specific 454 bp PCR product for R-tubulin. A radiolabelled nucleotide was included in this reaction, the PCR products were separated on a 2% agarose gel and the intensity of each band was quantitated by a Phosphoimager (Molecular Dynamics). FIG. 5A shows an ethidium bromide stained agarose gel with the separated quantitative PCR products and is representative of the typical results observed.

Figure 5B:
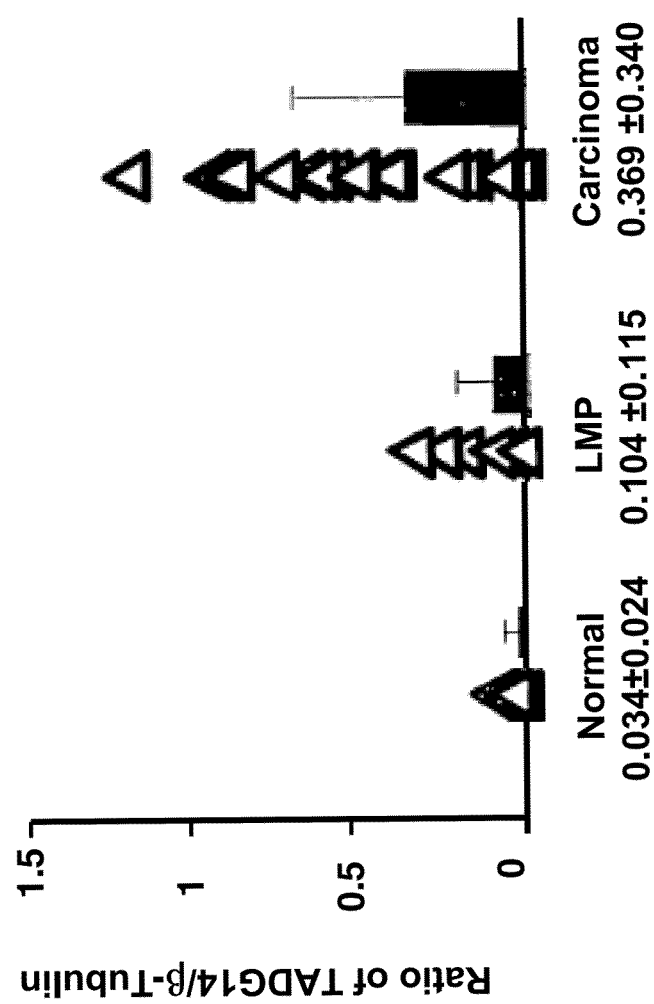
Figure 6:
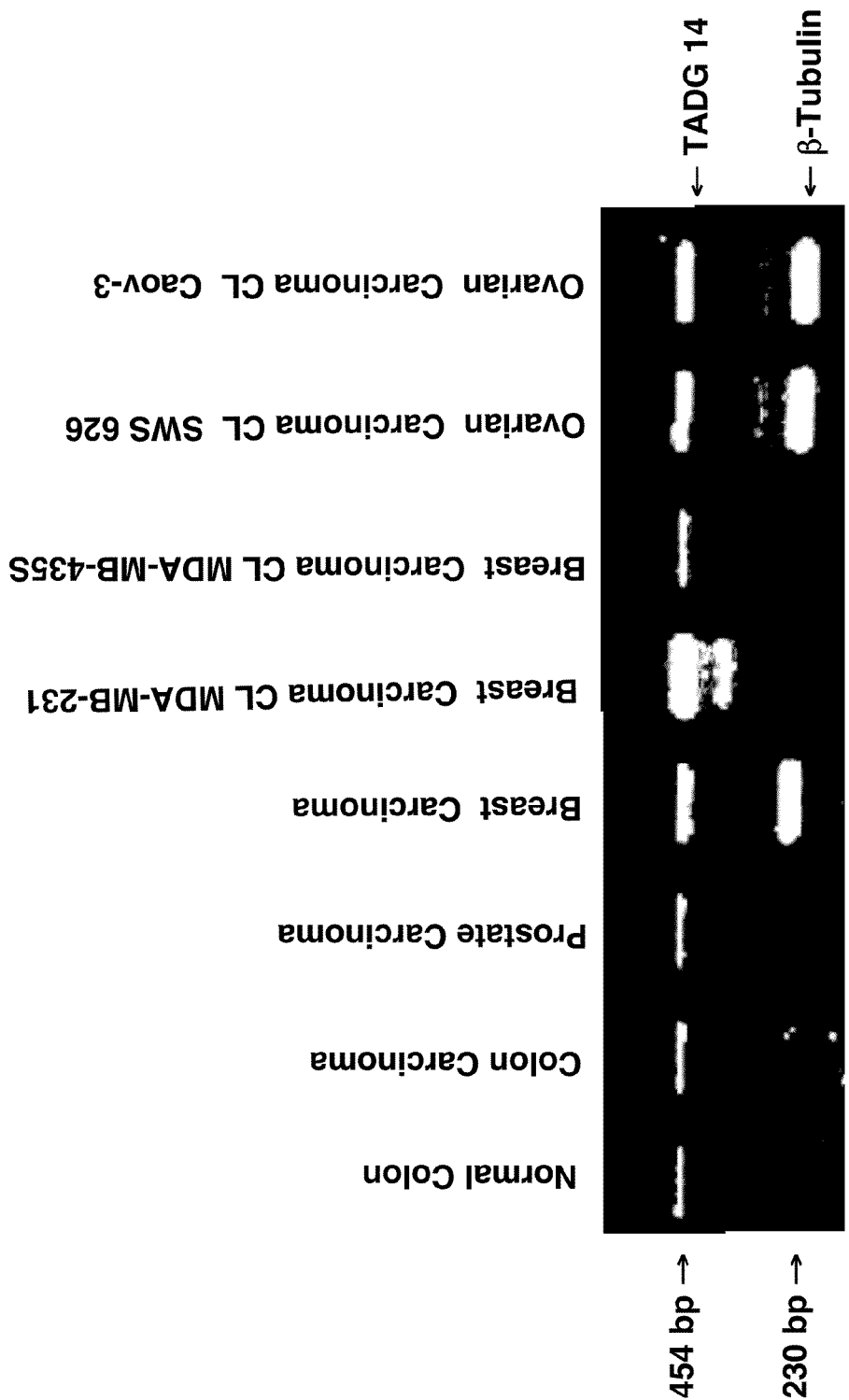
FIG. 6 shows the TADG-14 expression in tumors and cell lines.

The ratio of the TADG-14 PCR product to that of β-tubulin (mean±SD) was calculated for normal ovary samples which all showed relatively low expression levels (0.034±0.024). TADG-14 overexpression was defined as exceeding the mean of the ratio of TADG-14 to β-tubulin for normal samples by greater than 2 standard deviations (SD). TADG-14 was found to be overexpressed in 4 of 10 LMP tumors (40%), and 20 of 30 ovarian carcinomas (67%) studied. For individual histologic subtypes of tumor, the expression ratio was 0.110±0.092 for serous LMP tumors, 0.096±0.142 for mucinous LMP tumors, 0.457±0.345 for serous carcinomas, 0.171±0.300 for mucinous carcinomas, 0.308±0.144 for clear cell carcinomas, and 0.485±0.325 for endometrioid carcinomas. Of the 30 ovarian carcinomas studied, 13 of 17 serous tumors, 1 of 7 mucinous tumors, 3 of 3 clear cell tumors and 3 of 3 endometrioid tumors overexpressed TADG-14 (FIG. 5B). These data are summarized in Table 1. Although not quantitated, transcripts for TADG-14 were also detectable in breast and colon carcinoma (FIG. 6).

TABLE 1

TADG-14 Overexpression by Tissue Subtype

| Tissue Type | TADG14 Overexpression |
| --- | --- |
| Normal | 0/10 (0%) |
| LMP | 4/10 (40%) |
| Serous | 3/6 (50%) |
| Mucinous | 1/4 (25%) |
| Carcinoma | 20/30 (67%) |
| Serous | 13/17 (76%) |
| Mucinous | 1/7 (14%) |
| Endometrioid | 3/3 (100%) |
| Clear Cell | 3/3 (100%) |

Figure 7:
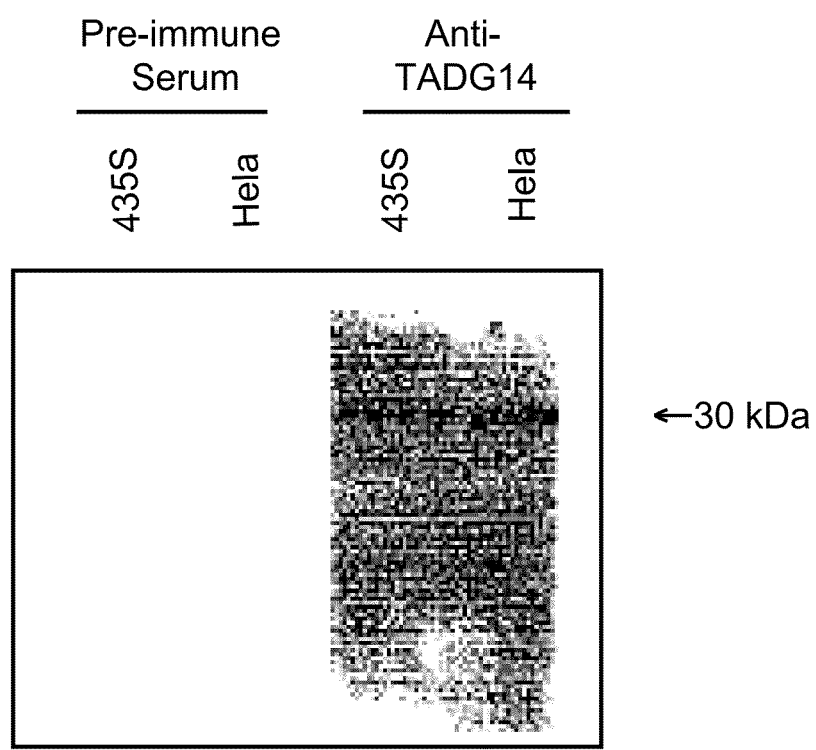
FIG. 7 shows Western blot analysis of TADG-14. Polyclonal antibodies were generated by immunization of rabbits with one of three poly-lysine linked multiple antigen peptides derived from the deduced amino acid sequence of TADG-14. For Western blot analysis, approximately 20 ug of MDA-MB-435S and HeLa cell lysates were separated on a 15% SDS-PAGE gel and electroblotted to PVDF at 100V for 40 minutes at 4° C. The blot was blocked overnight in Tris-buffered saline (TBS), pH 7.8 containing 0.2% non-fat milk. Primary antibody was added to the membrane at a dilution of 1:100 in 0.2% milk/TBS and incubated for 2 hours at room temperature. The blot was washed and incubated with 1:3000 dilution of alkaline-phosphatase conjugated goat and anti-rabbit IgG antibody (Bio-Rad) for one hour at room temperature. The blot was washed and incubated with a chemiluminescent substrate (Bio-Rad) before a 10-second exposure to X-ray film for visualization.

Immunogenic poly-lysine linked multiple antigen peptides were synthesized based on the deduced amino acid sequence of TADG-14 and used to immunize rabbits for the production of polyclonal antibodies. The antiserum raised to the peptide sequence LDWIKKIIGSKG (SEQ ID No. 16), near the carboxy terminal (AA #249-260), was used in Western blot analysis to determine if this antibody would recognize a protein of the predicted size of 28 kDa. Proteins from the HeLa cell line and the carcinoma derived MD-MBA-435S cell line were used in this experiment and it was found that the antibody recognized a single 30 kDa protein in both cell lines (FIG. 7, lanes 3 and 4). This size is within a reasonable range of the predicted molecular weight. As a negative control, duplicate HeLa and MD-MB435S lysates were examined with rabbit pre-immune serum (FIG. 7, lanes 1 and 2). More importantly, this experiment was reproducible with antisera to a peptide from a different region of TADG-14, suggesting that these cultured cancer cells produce the TADG-14 protein.

Figure 8A:
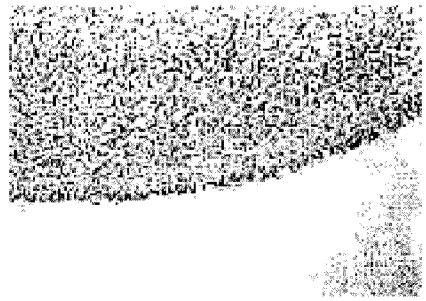
FIGS. 8A-8F show immunohistochemistry of TADG-14. Staining was with the TADG-14-1 antibody for normal ovary, two serous carcinomas, mucinous carcinoma, endometrioid carcinoma and clear cell carcinoma of the ovary (FIG. 8A, FIG. 8B, FIG. 8C, FIG. 8D, FIG. 8E and FIG. 8F, respectively). No staining was observed in normal ovary. The serous carcinoma shown in FIG. 8B has TADG-14 most strongly associated with the surface of the tumor, while in the serous tumor in FIG. 8C, TADG-14 was found in a granular form in an apparent secretion pathway. In mucinous carcinoma TADG-14 appears to be most highly expressed along the invasive front of the tumor. TADG-14 was secreted into the lumen of the glandular structure formed by the endometrioid carcinoma in FIG. 8E. The clear cell carcinoma stained in FIG. 8F shows diffuse staining throughout all tumor cells.
Figure 8D:
Figure 8B:
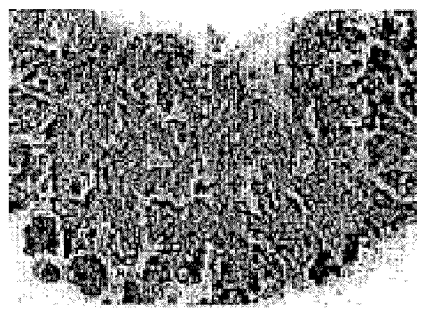
Figure 8E:
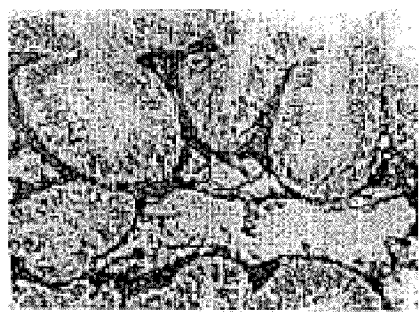
Figure 8C:
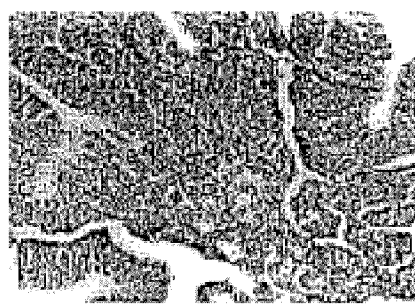
Figure 8F:

Immunohistochemical staining supported the data obtained by quantitative PCR and Northern blot. Using a TADG-14 peptide directed antibody, no staining was observed with normal ovarian tissue samples (FIG. 8A). However, intense staining was associated with tumor cells of all of the various histological subtypes of ovarian carcinoma examined. For serous carcinoma (FIGS. 8B and 8C) the antigen appears to be associated with tumor cells in the form of granules. These granular structures may be intermediates in the pathway that ultimately leads to secretion of TADG-14. In mucinous and clear cell carcinoma samples (FIGS. 8D and 8F respectively), TADG-14 is highly associated with the tumor cells. In endometrioid carcinoma (FIG. 8E), the antigen is most prevalent in the glandular lumen formed by the tumor cells.

The lethality of neoplastic cells lies in their ability to proliferate abnormally and invade normal host tissues. Malignancies employ proteases to provide a variety of services that assist in the process of tumor progression including activation of growth and angiogenic factors and to provide the basis for invasion and metastasis. In the process of studying these enzymes, overexpression of known proteases such as hepsin and SCCE have been identified. In the present study, a cDNA encoding a novel serine protease, TADG14, was cloned. This protease was found to be very highly expressed in 67% (20/30) of ovarian carcinomas studied, whereas it was undetected in normal ovarian tissue. The TADG14 transcript was also not detectable in any of 50 normal human tissues studied. On prolonged Northern blot exposure, extremely low levels of TADG-14 were detected in normal kidney, breast and lung. This suggests the possibility that this gene is under the control of a promoter that is most active in ovarian tumors, and it may be possible to exploit this for therapeutic means. Unfortunately, TADG14 expression can be detected in other types of cancer including prostate, breast and colon. This may limit the usefulness of TADG14 as a potential diagnostic maker for ovarian carcinoma, but it in no way detracts from the usefulness of this molecule as a target for cancer therapy or the usefulness of the TADG14 promoter in gene therapy applications.

At the nucleotide level, TADG14 mRNA resembles the recently cloned human neuropsin transcript with obvious differences residing in the 5' and 3' UTRS. TADG14 mRNA contains 491 bases of 5' UTR that were not found in human neuropsin. Also, the nucleotides preceding the poly (A) tail in the 3' UTR are not homologous. A 0.9kb transcript for human neuropsin was identified in cultured keratinocytes but not in normal hippocampus. Also, it was not identified as being associated with tumors. At the amino acid level, TADG14 is identical to human neuropsin.

Among other known proteases, TADG14 most closely resembles the mouse protease known as neuropsin, which was originally cloned from mouse hippocampus, and subsequently implicated in neuronal plasticity (17). If TADG14 functions in a manner similar to mouse neuropsin, it may be capable of restructuring the three-dimensional architecture of a tumor allowing for shedding of tumor cells or invasion of normal host tissues by degrading fibronectin (18). In support of this, immunohistochemical staining of ovarian tumors revealed that TADG14 is highly associated with tumor cells and the cells near the invasive fronts of tumor. Therefore, TADG14 could be an important target for the inhibition of tumor progression.

Most importantly, the five-year survival rate for ovarian cancer patients remains below 50% because of an inability to diagnose this disease at an early stage. TADG14 contains a secretion signal sequence and immunohistochemical data suggest that TADG14 is secreted. In addition, by Northern blot and RNA dot blot analyses, TADG14 appears only in abundance in tumor tissues. As a result of this, it may be possible to design assays based on the detection of this protein for the early detection of ovarian cancer. Currently, the best available ovarian cancer tumor marker is CA125. However, due to high endogenous circulating levels of this antigen, the signal to noise ratio limits its usefulness as a diagnostic tool. Therefore, TADG14, due to its limited expression in other tissues and potential for being present in the circulation of tumor bearing patients, may prove to be a useful tool for early detection of ovarian cancer, especially the most prevalent serous cystadenocarcinoma subtype.

EXAMPLE 2

Peptide Ranking Analysis for Vaccine Candidates

For vaccine or immune stimulation, individual 9-mers to 11-mers of the TADG-14 protein were examined to rank the binding of individual peptides to the top 8 haplotypes in the general population (Parker et al., (1994)). Table 2 shows the peptide ranking based upon the predicted half-life of each peptide's binding to a particular HLA allele. A larger half-life indicates a stronger association with that peptide and the particular HLA molecule. The TADG-14 peptides that strongly bind to an HLA allele are putative immunogens, and are used to innoculate an individual against TADG-14.

TABLE 2

TADG-14 Peptide Ranking

| HLA Type & Ranking | Start | Peptide | Predicted Dissociation$_{1/2}$ | SEQ ID No. |
|---|---|---|---|---|
| HLA A0201 | | | | |
| 1 | 55 | QLLCGGVLV | 257.342 | 17 |
| 2 | 15 | LLLLGGAWA | 171.868 | 18 |
| 3 | 60 | GVLVGGNWV | 123.846 | 19 |
| 4 | 61 | VLVGGNWVL | 111.672 | 20 |
| 5 | 49 | ALFQGQQLL | 79.041 | 21 |
| 6 | 10 | KTWMFLLLL | 75.331 | 22 |
| 7 | 131 | SLGSKVKPI | 23.995 | 23 |
| 8 | 122 | MLLQLRDQA | 15.312 | 24 |
| 9 | 124 | LQLRDQASL | 13.624 | 25 |
| 10 | 170 | TLNCAEVKI | 10.433 | 26 |
| HLA A0205 | | | | |
| 1 | 124 | LQLRDQASL | 28.560 | 25 |
| 2 | 10 | KTWMFLLLL | 25.200 | 22 |
| 3 | 49 | ALFQGQQLL | 21.000 | 21 |
| 4 | 208 | CQGDSGGPL | 16.800 | 27 |
| 5 | 54 | QQLLCGGVL | 16.800 | 28 |
| 6 | 61 | VLVGGNWVL | 14.280 | 20 |
| 7 | 60 | GVLVGGNWV | 12.000 | 19 |
| 8 | 62 | LVGGNWVLT | 6.800 | 29 |
| 9 | 55 | QLLCGGVLV | 6.000 | 17 |
| 10 | 191 | QITDGMVCA | 3.000 | 30 |
| HLA A1 | | | | |
| 1 | 173 | CAEVKIFPQ | 4.500 | 31 |
| 2 | 83 | LGDHSLQNK | 2.500 | 32 |
| 3 | 183 | KCEDAYPGQ | 1.800 | 33 |
| 4 | 192 | ITDGMVCAG | 1.250 | 34 |
| 5 | 71 | AAHCKKPKY | 1.000 | 35 |
| 6 | 113 | DVEDHNHDL | 0.900 | 36 |
| 7 | 229 | GSDPCGRSD | 0.750 | 37 |
| 8 | 111 | SSDVEDHNH | 0.750 | 38 |
| 9 | 28 | AQEDKVLGG | 0.675 | 39 |
| 10 | 217 | VCDGALQGI | 0.500 | 40 |

TABLE 2-continued

TADG-14 Peptide Ranking

| HLA Type & Ranking | Start | Peptide | Predicted Dissociation$_{1/2}$ | SEQ ID No. |
|---|---|---|---|---|
| HLA A24 | | | | |
| 1 | 241 | VYTNICRYL | 280.000 | 41 |
| 2 | 247 | RYLDWIKKI | 198.000 | 42 |
| 3 | 10 | KTWMFLLLL | 8.000 | 22 |
| 4 | 7 | RAAKTWMFL | 8.000 | 43 |
| 5 | 42 | HSQPWQAAL | 7.200 | 44 |
| 6 | 48 | AALFQGQQL | 7.200 | 45 |
| 7 | 113 | DVEDHNHDL | 7.200 | 36 |
| 8 | 54 | QQLLCGGVL | 6.000 | 28 |
| 9 | 214 | GPLVCDGAL | 6.000 | 46 |
| 10 | 61 | VLVGGNWVL | 6.000 | 20 |
| HLA B7 | | | | |
| 1 | 80 | TVRLGDHSL | 200.000 | 47 |
| 2 | 5 | RPRAAKTWM | 200.000 | 48 |
| 3 | 214 | GPLVCDGAL | 80.000 | 46 |
| 4 | 48 | AALFQGQQL | 36.000 | 45 |
| 5 | 8 | AAKTWMFLL | 36.000 | 49 |
| 6 | 3 | RPRPRAAKT | 20.000 | 50 |
| 7 | 162 | SPRENFPDT | 20.000 | 51 |
| 8 | 188 | YPGQITDGM | 20.000 | 52 |
| 9 | 7 | RAAKTWMFL | 12.000 | 43 |
| 10 | 49 | ALFQGQQLL | 12.000 | 21 |
| HLA B8 | | | | |
| 1 | 133 | GSKVKPISL | 80.000 | 53 |
| 2 | 8 | AAKTWMFLL | 16.000 | 49 |
| 3 | 3 | RPRPRAAKT | 8.000 | 50 |
| 4 | 80 | TVRLGDHSL | 4.000 | 47 |
| 5 | 73 | HCKKPKYTV | 2.400 | 54 |
| 6 | 131 | SLGSKVKPI | 2.000 | 23 |
| 7 | 5 | RPRAAKTWM | 2.000 | 48 |
| 8 | 162 | SPRENFPDT | 1.200 | 51 |
| 9 | 214 | GPLVCDGAL | 0.800 | 46 |
| 10 | 179 | FPQKKCEDA | 0.800 | 55 |
| HLA B2702 | | | | |
| 1 | 234 | GRSDKPGVY | 200.000 | 56 |
| 2 | 246 | CRYLDWIKK | 20.000 | 57 |
| 3 | 101 | VQSIPHPCY | 20.000 | 58 |

TABLE 2-continued

TADG-14 Peptide Ranking

| HLA Type & Ranking | Start | Peptide | Predicted Dissociation$_{1/2}$ | SEQ ID No. |
|---|---|---|---|---|
| 4 | 43 | SQPWQAALF | 20.000 | 59 |
| 5 | 6 | PRAAKTWMF | 20.000 | 60 |
| 6 | 26 | SRAQEDKVL | 18.000 | 61 |
| 7 | 126 | LRDQASLGS | 10.000 | 62 |
| 8 | 149 | GQKCTVSGW | 10.000 | 63 |
| 9 | 124 | LQLRDQASL | 6.000 | 25 |
| 10 | 54 | QQLLCGGVL | 6.000 | 28 |
| HLA B4403 | | | | |
| 1 | 96 | QEIPVVQSI | 180.000 | 64 |
| 2 | 71 | AAHCKKPKY | 13.500 | 35 |
| 3 | 171 | LNCAEVKIF | 4.500 | 65 |
| 4 | 184 | CEDAYPGQI | 4.000 | 66 |
| 5 | 114 | VEDHNHDLM | 4.000 | 67 |
| 6 | 101 | VQSIPHPCY | 2.250 | 68 |
| 7 | 236 | SDKPGVYTN | 1.800 | 69 |
| 8 | 164 | RENFPDTLN | 1.800 | 70 |
| 9 | 174 | AEVKIFPQK | 1.600 | 71 |
| 10 | 43 | SQPWQAALF | 1.500 | 59 |

EXAMPLE 3

TADG-14 Variant

Because members of the serine protease family are highly expressed and secreted by tumors, they offer potential targets for both diagnosis and therapy. While many of these enzymes are predominantly tumor produced, there is often some level of expression in a limited number of normal tissues. To further enhance the potential for more specific tumor diagnosis and targeting, it would be helpful to provide unique sequences which might be included in the enzyme families. The present example discloses a transcription variant of TADG-14. The TADG-14 variant includes unique intron sequence which could provide potential specificity to the recognition of TADG-14 in tumor.

Data presented above indicated TADG-14 overexpression in ovarian tumors. Kishi et al. confirmed the overexpression of KLK8 (Neuropsin/Ovasin), which was described as TADG-14 here, as highly overexpressed in the ascites fluid of ovarian cancer patients and presented at elevated levels in serum of 62% of ovarian cancer patients.

Figure 9:
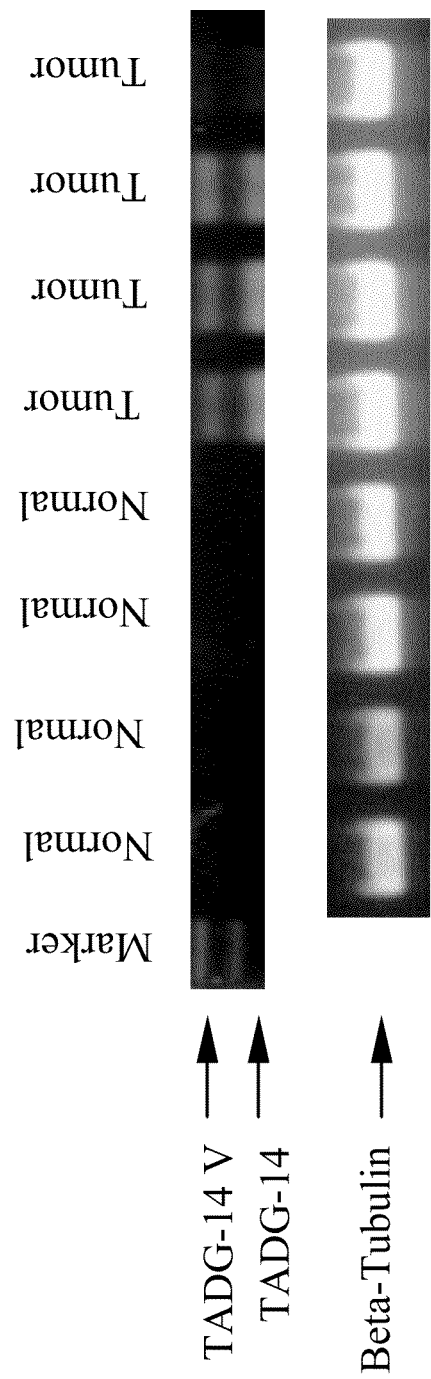
FIG. 9 shows the expression of TADG-14 and T-14 variant in normal ovary and ovarian carcinoma.

When the complete transcript of the TADG-14 gene was examined for potential variants, one variant was detected which included intron sequence between exon 2 and exon 3. Using primers from exon 1 and exon 3 of TADG-14, a PCR band larger than the expected exon 2-exon 3 band was detected in ovarian tumor cells (FIG. 9). The sequence of this TADG-14 variant was confirmed. It included all intron 2 sequence and it could be translated into an extended amino acid sequence which presumably would still have protease activity (FIGS. 10-11). The addition of the intron sequence and the subsequent translation into additional amino acid sequence provides an opportunity to add unique specificity for diagnostic detection and/or targeting of tumor therapy. This variant was expressed in 5 out of 6 ovarian carcinomas examined. Normal ovary cells did not express this TADG-14 variant. On examination of the EST database for taq sequence for intron 2 of TADG-14, only one expressed sequence was detected in an adenocarcinoma cell line of the ovary. These data thus suggest a potential role for this TADG-14 variant in both detecting and targeting of ovarian carcinomas.

Sense and antisense primers were made to exons 2 and 3 of TADG-14 (TADG-14 Sense, 5'-CGA CCT CGT GCG GCC AAG ACG-3', SEQ ID NO. 73; TADG-14 Antisense, 5'-CAG CTG TAA GGA CCC AGT TGC-3', SEQ ID NO. 74). All PCR was run in 20 ul reactions consisting of ovarian tumor cDNA derived from 50 ng of mRNA, 5 pmol each of sense and antisense primers, 0.2 mmol of dNTPs, 2.5mmol of MgCl$_2$ and 1U of Taq polymerase in 1× buffer. This mixture was subjected to 1.5 minutes of denaturation at 94° C. followed by 35 cycles of PCR consisting of the following: denaturation for 30 seconds at 94° C., 30 seconds of annealing at the appropriate temperature for each primer set, and 1 minute of extension at 72° C. with an additional 7 minutes of extension on the last cycle.

The following references were cited herein:

1. Neurath, H. The Diversity of Proteolytic Enzymes. In: R. J. Beynon and J. S. Bond (eds.), pp. 1-13, Proteolytic enzymes, Oxford: IRL Press, 1989
2. Liotta et al., Cell, 64: 327-336, 1991.
3. Duffy, Clin. Exp. Metastasis, 10: 145-155, 1992.
4. Tryggvason et al., Biochem. Biophys. Acta., 907: 191-217, 1987.
5. Monsky et al., Cancer Res., 53: 3159-3164, 1993.
6. Powell et al., Cancer Res., 53: 417-422, 1993.
7. McCormack et al., Urology, 45: 729-744, 1995.
8. Sakanari et al., Proc. Natl. Acad. Sci. U.S.A., 86: 4863-4867, 1989.
9. Tanimoto et al., Cancer Res., 57: 2884-2887, 1997.
10. Tanimoto et al., *Cancer,* 1998.
11. Evans et al., Biochemistry, 27: 3124-3129, 1988.
12. Watt et al., Proc. Natl. Acad. Sci. U.S.A., 83: 3166-3120, 1986.
13. Anisowicz et al., Mol. Medicine. 2: 624-636, 1996.
14. Chen et al., J. Neuroscience. 15: 5088-5097, 1995.
15. Yoshida et al., Gene 213: 9-16, 1998.
16. Shigemasa et al., J. Soc. Gynecol. Invest. 4: 95-102, 1997.
17. Suzuki et al., Neuroscience Res., 23: 345-351, 1995.
18. Shimizu et al., J Biol Chem, 273: 11189-11196, 1998.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

What is claimed is:

1. An isolated antibody or immunologically-active fragment thereof that specifically binds to a sequence shown in SEQ ID NO: 7.

2. The antibody of claim 1, wherein the antibody is a monoclonal antibody, a polyclonal antibody or a chimeric antibody.

3. The antibody of claim 2, wherein the antibody is a monoclonal antibody and the sequence is a recombinant protein.

4. An isolated antibody or immunologically-active fragment thereof that specifically binds to a sequence shown in SEQ ID NO: 75.

5. The antibody of claim 4, wherein the antibody is a monoclonal antibody, a polyclonal antibody or a chimeric antibody.

6. The antibody of claim 5, wherein the antibody is a monoclonal antibody and the sequence is a recombinant protein.

7. A kit comprising the antibody or immunologically-active fragment thereof of claim 4 and a detectable label linked thereto.

8. A compound, comprising:
   the antibody of claim 1; and
   a targeting moiety and a therapeutic moiety each linked to said antibody.

9. A kit comprising the antibody or immunologically-active fragment thereof of claim 4.

10. A compound, comprising:
   the antibody of claim 4; and
   a targeting moiety and a therapeutic moiety each linked to said antibody.

* * * * *

SEQUENCE LISTING

<160> NUMBER OF SEQ ID NOS: 75

<210> SEQ ID NO 1
<211> LENGTH: 144
<212> TYPE: PRT
<213> ORGANISM: unknown
<220> FEATURE:
<221> NAME/KEY: DOMAIN
<223> OTHER INFORMATION: Amino acid sequence of Protease m (Prom)
      catalytic domain

<400> SEQUENCE: 1

Trp Val Leu Thr Ala Ala His Cys Lys Lys Pro Asn Leu Gln Val
1               5                   10                  15

Phe Leu Glu Lys His Asn Leu Arg Gln Arg Glu Ser Ser Gln Glu
                20                  25                  30

Gln Ser Ser Val Val Arg Ala Val Ile His Pro Asp Tyr Asp Ala
                35                  40                  45

Ala Ser His Asp Gln Asp Ile Met Leu Leu Arg Leu Ala Arg Pro
                50                  55                  60

Ala Lys Leu Ser Glu Leu Ile Gln Pro Leu Pro Leu Glu Arg Asp
                65                  70                  75

Cys Ser Ala Asn Thr Thr Ser Cys His Ile Leu Gly Trp Gly Lys
                80                  85                  90

Thr Ala Asp Gly Asp Phe Pro Asp Thr Ile Gln Cys Ala Tyr Ile
                95                  100                 105

His Leu Val Ser Arg Glu Glu Cys Glu His Ala Tyr Pro Gly Gln
                110                 115                 120

Ile Thr Gln Asn Met Leu Cys Ala Gln Asp Glu Lys Tyr Gly Lys
                125                 130                 135

Asp Ser Cys Gln Gly Asp Ser Gly Gly
                140

<210> SEQ ID NO 2
<211> LENGTH: 148
<212> TYPE: PRT
<213> ORGANISM: Homo sapiens
<220> FEATURE:
<221> NAME/KEY: DOMAIN
<223> OTHER INFORMATION: Amino acid sequence of TADG-14 catalytic domain

<400> SEQUENCE: 2

Trp Val Val Thr Ala Ala His Cys Lys Lys Pro Lys Tyr Thr Val
1               5                   10                  15

Arg Leu Gly Asp His Ser Leu Gln Asn Lys Asp Gly Pro Glu Gln
                20                  25                  30

Glu Ile Pro Val Val Gln Ser Ile Pro His Pro Cys Tyr Asn Ser
                35                  40                  45

Ser Asp Val Glu Asp His Asn His Asp Leu Met Leu Leu Gln Leu
                50                  55                  60

Arg Asp Gln Ala Ser Leu Gly Ser Lys Val Lys Pro Ile Ser Leu
                65                  70                  75

Ala Asp His Cys Thr Gln Pro Gly Gln Asn Cys Thr Val Ser Gly
                80                  85                  90

Trp Gly Thr Val Thr Ser Pro Arg Glu Asn Phe Pro Asp Thr Leu
                95                  100                 105

Asn Cys Ala Glu Val Lys Ile Phe Pro Gln Lys Lys Cys Glu Asp
                110                 115                 120

-continued

```
Ala Tyr Pro Gly Gln Ile Thr Asp Gly Met Val Cys Ala Gly Ser
                125                 130                 135

Ser Lys Gly Ala Asp Thr Cys Gln Gly Asp Ser Gly Gly
                140                 145

<210> SEQ ID NO 3
<211> LENGTH: 146
<212> TYPE: PRT
<213> ORGANISM: unknown
<220> FEATURE:
<221> NAME/KEY: DOMAIN
<223> OTHER INFORMATION: Amino acid sequence of trypsin like serine
      protease (Try1) catalytic domain

<400> SEQUENCE: 3

Trp Val Val Ser Ala Gly His Cys Tyr Lys Ser Arg Ile Gln Val
1               5                   10                  15

Arg Leu Gly Glu His Asn Ile Glu Val Leu Glu Gly Asn Glu Gln
                20                  25                  30

Phe Ile Asn Ala Ala Lys Ile Ile Arg His Pro Gln Tyr Asp Arg
                35                  40                  45

Lys Thr Leu Asn Asn Asp Ile Met Leu Ile Lys Leu Ser Ser Arg
                50                  55                  60

Ala Val Ile Asn Ala Arg Val Ser Thr Ile Ser Leu Pro Thr Ala
                65                  70                  75

Pro Pro Ala Thr Gly Thr Lys Cys Leu Ile Ser Gly Trp Gly Asn
                80                  85                  90

Thr Ala Ser Ser Gly Ala Asp Tyr Pro Asp Glu Leu Gln Cys Leu
                95                  100                 105

Asp Ala Pro Val Leu Ser Gln Ala Lys Cys Glu Ala Ser Tyr Pro
                110                 115                 120

Gly Lys Ile Thr Ser Asn Met Phe Cys Val Gly Phe Leu Glu Gly
                125                 130                 135

Gly Lys Asp Ser Cys Gln Gly Asp Ser Gly Gly
                140                 145

<210> SEQ ID NO 4
<211> LENGTH: 144
<212> TYPE: PRT
<213> ORGANISM: unknown
<220> FEATURE:
<221> NAME/KEY: DOMAIN
<223> OTHER INFORMATION: Amino acid sequence of stratum corneum
      chymotryptic enzyme (scce) catalytic domain

<400> SEQUENCE: 4

Trp Val Leu Thr Ala Ala His Cys Lys Met Asn Glu Tyr Thr Val
1               5                   10                  15

His Leu Gly Ser Asp Thr Leu Gly Asp Arg Arg Ala Gln Arg Ile
                20                  25                  30

Lys Ala Ser Lys Ser Phe Arg His Pro Gly Tyr Ser Thr Gln Thr
                35                  40                  45

His Val Asn Asp Leu Met Leu Val Lys Leu Asn Ser Gln Ala Arg
                50                  55                  60

Leu Ser Ser Met Val Lys Lys Val Arg Leu Pro Ser Arg Cys Glu
                65                  70                  75

Pro Pro Gly Thr Thr Cys Thr Val Ser Gly Trp Gly Thr Thr Thr
                80                  85                  90

Ser Pro Asp Val Thr Phe Pro Ser Asp Leu Met Cys Val Asp Val
```

```
                    95                  100                 105
Lys Leu Ile Ser Pro Gln Asp Cys Thr Lys Val Tyr Lys Asp Leu
            110                 115                 120
Leu Glu Asn Ser Met Leu Cys Ala Gly Ile Pro Asp Ser Lys Lys
            125                 130                 135
Asn Ala Cys Asn Gly Asp Ser Gly Gly
            140

<210> SEQ ID NO 5
<211> LENGTH: 159
<212> TYPE: PRT
<213> ORGANISM: unknown
<220> FEATURE:
<221> NAME/KEY: DOMAIN
<223> OTHER INFORMATION: Amino acid sequence of hepsin (heps) catalytic
      domain

<400> SEQUENCE: 5

Trp Val Leu Thr Ala Ala His Cys Phe Pro Glu Arg Asn Arg Val
1               5                   10                  15
Leu Ser Arg Trp Arg Val Phe Ala Gly Ala Val Ala Gln Ala Ser
                20                  25                  30
Pro His Gly Leu Gln Leu Gly Val Gln Ala Val Val Tyr His Gly
            35                  40                  45
Gly Tyr Leu Pro Phe Arg Asp Pro Asn Ser Glu Glu Asn Ser Asn
            50                  55                  60
Asp Ile Ala Leu Val His Leu Ser Ser Pro Leu Pro Leu Thr Glu
            65                  70                  75
Tyr Ile Gln Pro Val Cys Leu Pro Ala Ala Gly Gln Ala Leu Val
            80                  85                  90
Asp Gly Lys Ile Cys Thr Val Thr Gly Trp Gly Asn Thr Gln Tyr
            95                  100                 105
Tyr Gly Gln Gln Ala Gly Val Leu Gln Glu Ala Arg Val Pro Ile
            110                 115                 120
Ile Ser Asn Asp Val Cys Asn Gly Ala Asp Phe Tyr Gly Asn Gln
            125                 130                 135
Ile Lys Pro Lys Met Phe Cys Ala Gly Tyr Pro Glu Gly Gly Ile
            140                 145                 150
Asp Ala Cys Gln Gly Asp Ser Gly Gly
155

<210> SEQ ID NO 6
<211> LENGTH: 1343
<212> TYPE: DNA
<213> ORGANISM: Homo sapiens
<220> FEATURE:
<223> OTHER INFORMATION: Nucleotide sequence encoding Tumor Antigen
      Derived Gene-14 (TADG-14) protein

<400> SEQUENCE: 6
ctgtagcagg cagagcttac caagtctctc cgaactcaaa tggaagaaat          50
accttatgaa tgtaagaatg tagggggtca tggcttgtaa tttacacagt         100
gtaaatgaaa ccatcctaga ggattatgag gaatcctttc tatgtgattt         150
tcaatcatag caagcaagaa aggctccagt gtcaaggtag ttcagctctt         200
acaggatata aaacagtcca tacttgagag aaaaaactta gatctgagtg         250
atggaatgtg aagcaaatct ttcaaaatca gtagacattt cttggacata         300
aaacacagat gaggaaaggg cttcaaatta gaagttacgt aatcaccatc         350
```

```
agaaagttca tgtttggtaa attctgttac tagaaatgta ggaaattcag          400
gtatagcttt gaatcccaat tacacattgg tcagtgggaa aactaagggc          450
ctccaacagg caaattcagg gaggataggt ttcagggaat gccctggatt          500
ctggaagacc tcaccatggg acgccccga cctcgtgcgg ccaagacgtg           550
gatgttcctg ctcttgctgg ggggagcctg gcaggacac tccagggcac           600
aggaggacaa ggtgctgggg ggtcatgagt gccaacccca ttcgcagcct          650
tggcaggcgg ccttgttcca gggccagcaa ctactctgtg cggtgtcct           700
tgtaggtggc aactgggtcc ttacagctgc ccactgtaaa aaaccgaaat          750
acacagtacg cctgggagac acagcctac agaataaaga tggcccagag           800
caagaaatac ctgtggttca gtccatccca caccctgct acaacagcag           850
cgatgtggag gaccacaacc atgatctgat gcttcttcaa ctgcgtgacc          900
aggcatccct ggggtccaaa gtgaagccca tcagcctggc agatcattgc          950
acccagcctg ccagaagtg caccgtctca ggctggggca ctgtcaccag          1000
tccccgagag aatttcctg acactctcaa ctgtgcagaa gtaaaaatct          1050
ttccccagaa gaagtgtgag gatgcttacc ggggcagat cacagatggc          1100
atggtctgtg caggcagcag caaaggggct gacacgtgcc agggcgattc         1150
tggaggcccc ctggtgtgtg atggtgcact ccagggcatc acatcctggg         1200
gctcagaccc ctgtgggagg tccgacaaac tggcgtcta taccaacatc          1250
tgccgctacc tggactggat caagaagatc ataggcagca agggctgatt         1300
ctaggataag cactagatct cccttaataa actcacggaa ttc                1343
```

<210> SEQ ID NO 7  
<211> LENGTH: 260  
<212> TYPE: PRT  
<213> ORGANISM: Homo sapiens  
<220> FEATURE:  
<223> OTHER INFORMATION: Amino acid sequence of TADG-14 protein

<400> SEQUENCE: 7

```
Met Gly Arg Pro Arg Pro Arg Ala Ala Lys Thr Trp Met Phe Leu
1               5                   10                  15

Leu Leu Leu Gly Gly Ala Trp Ala Gly His Ser Arg Ala Gln Glu
                20                  25                  30

Asp Lys Val Leu Gly Gly His Glu Cys Gln Pro His Ser Gln Pro
                35                  40                  45

Trp Gln Ala Ala Leu Phe Gln Gly Gln Gln Leu Leu Cys Gly Gly
                50                  55                  60

Val Leu Val Gly Gly Asn Trp Val Leu Thr Ala Ala His Cys Lys
                65                  70                  75

Lys Pro Lys Tyr Thr Val Arg Leu Gly Asp His Ser Leu Gln Asn
                80                  85                  90

Lys Asp Gly Pro Glu Gln Glu Ile Pro Val Val Gln Ser Ile Pro
                95                  100                 105

His Pro Cys Tyr Asn Ser Ser Asp Val Glu Asp His Asn His Asp
                110                 115                 120

Leu Met Leu Leu Gln Leu Arg Asp Gln Ala Ser Leu Gly Ser Lys
                125                 130                 135

Val Lys Pro Ile Ser Leu Ala Asp His Cys Thr Gln Pro Gly Gln
                140                 145                 150
```

```
Lys Cys Thr Val Ser Gly Trp Gly Thr Val Thr Ser Pro Arg Glu
            155                 160                 165

Asn Phe Pro Asp Thr Leu Asn Cys Ala Glu Val Lys Ile Phe Pro
            170                 175                 180

Gln Lys Lys Cys Glu Asp Ala Tyr Pro Gly Gln Ile Thr Asp Gly
            185                 190                 195

Met Val Cys Ala Gly Ser Ser Lys Gly Ala Asp Thr Cys Gln Gly
            200                 205                 210

Asp Ser Gly Gly Pro Leu Val Cys Asp Gly Ala Leu Gln Gly Ile
            215                 220                 225

Thr Ser Trp Gly Ser Asp Pro Cys Gly Arg Ser Asp Lys Pro Gly
            230                 235                 240

Val Tyr Thr Asn Ile Cys Arg Tyr Leu Asp Trp Ile Lys Lys Ile
            245                 250                 255

Ile Gly Ser Lys Gly
            260

<210> SEQ ID NO 8
<211> LENGTH: 799
<212> TYPE: DNA
<213> ORGANISM: Mus musculus
<220> FEATURE:
<223> OTHER INFORMATION: Nucleotide sequence of mouse neuropsin
      homologous to TADG-14

<400> SEQUENCE: 8
agaggccacc atgggacgcc cccaccctg tgcaatccag ccgtggatcc         50
ttctgcttct gttcatggga gcgtgggcag ggctcaccag agctcagggc        100
tccaagatcc tggaaggtcg agagtgtata ccccactccc agccttggca        150
ggcagccttg ttccagggcg agagactgat ctgtgggggt gtcctggttg        200
gagacagatg ggtcctcacg gcagcccact gcaaaaaaca gaagtactcc        250
gtgcgtctgg gtgatcatag cctccagagc agagatcagc cggagcagga        300
gatccaggtg gctcagtcta tccagcatcc ttgctacaac aacagcaacc        350
cagaagatca cagtcacgat ataatgctca ttcgactgca gaactcagca        400
aacctcgggg acaaggtgaa gccggtccaa ctggccaatc tgtgtcccaa        450
agttggccag aagtgcatca tatcaggctg ggcactgtc accagccctc         500 aagagaactt tccaaacacc ctcaactgtg cggaagtgaa atctattcc         550 cagaacaagt gtgagagagc ctatccaggg aagatcaccg agggcatggt        600
ctgtgctggc agcagcaatg agctgacac gtgccaggt gactcaggag          650 gccctctggt gtgcgacggg atgctccagg gcatcacctc atggggctca        700 gaccccgtg ggaaacccga gaaacctgga gtctacacca aaatctgccg         750
ctacactacc tggatcaaga agaccatgga caacagggac tgatcctgg         799

<210> SEQ ID NO 9
<211> LENGTH: 799
<212> TYPE: DNA
<213> ORGANISM: Homo sapiens
<220> FEATURE:
<223> OTHER INFORMATION: Nucleotide sequence of TADG-14 homologous to
      mouse neuropsin

<400> SEQUENCE: 9
agacctcacc atgggacgcc cccgacctcg tgcggccaag acgtggatgt        50
```

```
tcctgctctt gctgggggga gcctgggcag gacactccag ggcacaggag        100
gacaaggtgc tgggggtca tgagtgccaa ccccattcgc agccttggca         150
ggcggccttg ttccagggcc agcaactact ctgtggcggt gtccttgtag        200
gtggcaactg ggtccttaca gctgcccact gtaaaaaacc gaaatacaca        250
gtacgcctgg gagaccacag cctacagaat aaagatggcc cagagcaaga        300
aatacctgtg gttcagtcca tcccacaccc ctgctacaac agcagcgatg        350
tggaggacca caaccatgat ctgatgcttc ttcaactgcg tgaccaggca        400
tccctggggt ccaaagtgaa gcccatcagc ctggcagatc attgcaccca        450
gcctggccag aagtgcaccg tctcaggctg gggcactgtc accagtcccc        500
gagagaattt tcctgacact ctcaactgtg cagaagtaaa aatctttccc        550
cagaagaagt gtgaggatgc ttacccgggg cagatcacag atggcatggt       600
ctgtgcaggc agcagcaaag gggctgacac gtgccagggc gattctggag        650
gccccctggt gtgtgatggt gcactccagg gcatcacatc ctggggctca       700 gaccctgtg ggaggtccga caaacctggc gtctatacca acatctgccg        750
ctacctggac tggatcaaga agatcatagg cagcaagggc tgattctag         799
```

<210> SEQ ID NO 10
<211> LENGTH: 260
<212> TYPE: PRT
<213> ORGANISM: Mus musculus
<220> FEATURE:
<223> OTHER INFORMATION: Amino acid sequence of mouse neuropsin
       homologous to TADG-14

<400> SEQUENCE: 10

Met Gly Arg Pro Pro Cys Ala Ile Gln Pro Trp Ile Leu Leu
1               5                  10                  15

Leu Leu Phe Met Gly Ala Trp Ala Gly Leu Thr Arg Ala Gln Gly
            20                  25                  30

Ser Lys Ile Leu Glu Gly Arg Glu Cys Ile Pro His Ser Gln Pro
            35                  40                  45

Trp Gln Ala Ala Leu Phe Gln Gly Glu Arg Leu Ile Cys Gly Gly
            50                  55                  60

Val Leu Val Gly Asp Arg Trp Val Leu Thr Ala Ala His Cys Lys
65                  70                  75

Lys Gln Lys Tyr Ser Val Arg Leu Gly Asp His Ser Leu Gln Ser
            80                  85                  90

Arg Asp Gln Pro Glu Gln Glu Ile Gln Val Ala Gln Ser Ile Gln
            95                  100                 105

His Pro Cys Tyr Asn Asn Ser Asn Pro Glu Asp His Ser His Asp
            110                 115                 120

Ile Met Leu Ile Arg Leu Gln Asn Ser Ala Asn Leu Gly Asp Lys
            125                 130                 135

Val Lys Pro Val Gln Leu Ala Asn Leu Cys Pro Lys Val Gly Gln
            140                 145                 150

Lys Cys Ile Ile Ser Gly Trp Gly Thr Val Thr Ser Pro Gln Glu
            155                 160                 165

Asn Phe Pro Asn Thr Leu Asn Cys Ala Glu Val Lys Ile Tyr Ser
            170                 175                 180

Gln Asn Lys Cys Glu Arg Ala Tyr Pro Gly Lys Ile Thr Glu Gly
            185                 190                 195

```
Met Val Cys Ala Gly Ser Ser Asn Gly Ala Asp Thr Cys Gln Gly
                200                 205                 210

Asp Ser Gly Gly Pro Leu Val Cys Asp Gly Met Leu Gln Gly Ile
            215                 220                 225

Thr Ser Trp Gly Ser Asp Pro Cys Gly Lys Pro Glu Lys Pro Gly
            230                 235                 240

Val Tyr Thr Lys Ile Cys Arg Tyr Thr Thr Trp Ile Lys Lys Thr
            245                 250                 255

Met Asp Asn Arg Asp
            260

<210> SEQ ID NO 11
<211> LENGTH: 244
<212> TYPE: PRT
<213> ORGANISM: Homo sapiens
<220> FEATURE:
<223> OTHER INFORMATION: Amino acid sequence of human protease m
      (hProM); accession no. U62801

<400> SEQUENCE: 11

Met Lys Lys Leu Met Val Val Leu Ser Leu Ile Ala Ala Ala Trp
1               5                   10                  15

Ala Glu Glu Gln Asn Lys Leu Val His Gly Gly Pro Cys Asp Lys
                20                  25                  30

Thr Ser His Pro Tyr Gln Ala Ala Leu Thr Tyr Ser Gly His Leu
            35                  40                  45

Leu Cys Gly Gly Val Leu Ile His Pro Leu Trp Val Leu Thr Ala
            50                  55                  60

Ala His Cys Lys Lys Pro Asn Leu Gln Val Phe Leu Gly Lys His
            65                  70                  75

Asn Leu Arg Gly Arg Glu Ser Ser Gln Glu Gln Ser Ser Val Val
            80                  85                  90

Arg Ala Val Ile His Pro Asp Tyr Asp Ala Ala Ser His Asp Gln
            95                  100                 105

Asp Ile Met Leu Leu Arg Leu Ala Arg Pro Ala Lys Leu Ser Glu
            110                 115                 120

Leu Ile Gln Pro Leu Pro Leu Glu Arg Asp Cys Ser Ala Asn Thr
            125                 130                 135

Thr Ser Cys His Ile Leu Gly Trp Gly Lys Thr Ala Asp Gly Asp
            140                 145                 150

Phe Pro Asp Thr Ile Gln Cys Ala Tyr Ile His Leu Val Ser Arg
            155                 160                 165

Glu Glu Cys Glu His Ala Tyr Pro Gly Gln Ile Thr Gln Asn Met
            170                 175                 180

Leu Cys Ala Gly Asp Glu Lys Tyr Gly Lys Asp Ser Cys Gln Gly
            185                 190                 195

Asp Ser Gly Gly Pro Leu Val Cys Gly Asp His Ile Arg Gly Leu
            200                 205                 210

Val Ser Trp Gly Asn Ile Pro Cys Gly Ser Lys Glu Lys Pro Gly
            215                 220                 225

Val Tyr Thr Asn Val Cys Arg Tyr Thr Asn Trp Ile Gln Lys Thr
            230                 235                 240

Ile Gln Ala Lys

<210> SEQ ID NO 12
<211> LENGTH: 20
```

```
<212> TYPE: DNA
<213> ORGANISM: artificial sequence
<220> FEATURE:
<221> NAME/KEY: primer
<223> OTHER INFORMATION: Sense primer for TADG14 specific PCR

<400> SEQUENCE: 12
acagtacgcc tgggagacca                                                    20

<210> SEQ ID NO 13
<211> LENGTH: 20
<212> TYPE: DNA
<213> ORGANISM: artificial sequence
<220> FEATURE:
<221> NAME/KEY: primer
<223> OTHER INFORMATION: Anti-sense primer for TADG14 specific PCR

<400> SEQUENCE: 13
ctgagacggt gcaattctgg                                                    20

<210> SEQ ID NO 14
<211> LENGTH: 12
<212> TYPE: PRT
<213> ORGANISM: artificial sequence
<220> FEATURE:
<223> OTHER INFORMATION: Peptide sequence of immunogenic poly-lysine
      linked multiple antigen (T14-1) derived from
      TADG-14 used to produce polyclonal antibodies

<400> SEQUENCE: 14

Lys Tyr Thr Val Arg Leu Gly Asp His Ser Leu Gln
1               5                   10

<210> SEQ ID NO 15
<211> LENGTH: 12
<212> TYPE: PRT
<213> ORGANISM: artificial sequence
<220> FEATURE:
<223> OTHER INFORMATION: Peptide sequence of immunogenic poly-lysine
      linked multiple antigen (T14-2) derived from
      TADG-14 used to produce polyclonal antibodies

<400> SEQUENCE: 15

Gly His Glu Cys Gln Pro His Ser Gln Pro Trp Gln
1               5                   10

<210> SEQ ID NO 16
<211> LENGTH: 12
<212> TYPE: PRT
<213> ORGANISM: artificial sequence
<220> FEATURE:
<223> OTHER INFORMATION: Peptide sequence of immunogenic poly-lysine
      linked multiple antigen (T14-3) derived from
      TADG-14 used to produce polyclonal antibodies

<400> SEQUENCE: 16

Leu Asp Trp Ile Lys Lys Ile Ile Gly Ser Lys Gly
1               5                   10

<210> SEQ ID NO 17
<211> LENGTH: 9
<212> TYPE: PRT
<213> ORGANISM: Homo sapiens
<220> FEATURE:
<223> OTHER INFORMATION: Residues 55-63 of the TADG-14 protein

<400> SEQUENCE: 17

Gln Leu Leu Cys Gly Gly Val Leu Val
1               5
```

```
<210> SEQ ID NO 18
<211> LENGTH: 9
<212> TYPE: PRT
<213> ORGANISM: Homo sapiens
<220> FEATURE:
<223> OTHER INFORMATION: Residues 15-23 of the TADG-14 protein

<400> SEQUENCE: 18

Leu Leu Leu Leu Gly Gly Ala Trp Ala
1               5

<210> SEQ ID NO 19
<211> LENGTH: 9
<212> TYPE: PRT
<213> ORGANISM: Homo sapiens
<220> FEATURE:
<223> OTHER INFORMATION: Residues 60-68 of the TADG-14 protein

<400> SEQUENCE: 19

Gly Val Leu Val Gly Gly Asn Trp Val
1               5

<210> SEQ ID NO 20
<211> LENGTH: 9
<212> TYPE: PRT
<213> ORGANISM: Homo sapiens
<220> FEATURE:
<223> OTHER INFORMATION: Residues 61-69 of the TADG-14 protein

<400> SEQUENCE: 20

Val Leu Val Gly Gly Asn Trp Val Leu
1               5

<210> SEQ ID NO 21
<211> LENGTH: 9
<212> TYPE: PRT
<213> ORGANISM: Homo sapiens
<220> FEATURE:
<223> OTHER INFORMATION: Residues 49-57 of the TADG-14 protein

<400> SEQUENCE: 21

Ala Leu Phe Gln Gly Gln Gln Leu Leu
1               5

<210> SEQ ID NO 22
<211> LENGTH: 9
<212> TYPE: PRT
<213> ORGANISM: Homo sapiens
<220> FEATURE:
<223> OTHER INFORMATION: Residues 10-18 of the TADG-14 protein

<400> SEQUENCE: 22

Lys Thr Trp Met Phe Leu Leu Leu Leu
1               5

<210> SEQ ID NO 23
<211> LENGTH: 9
<212> TYPE: PRT
<213> ORGANISM: Homo sapiens
<220> FEATURE:
<223> OTHER INFORMATION: Residues 131-139 of the TADG-14 protein

<400> SEQUENCE: 23

Ser Leu Gly Ser Lys Val Lys Pro Ile
1               5
```

```
<210> SEQ ID NO 24
<211> LENGTH: 9
<212> TYPE: PRT
<213> ORGANISM: Homo sapiens
<220> FEATURE:
<223> OTHER INFORMATION: Residues 122-130 of the TADG-14 protein

<400> SEQUENCE: 24

Met Leu Leu Gln Leu Arg Asp Gln Ala
1               5

<210> SEQ ID NO 25
<211> LENGTH: 9
<212> TYPE: PRT
<213> ORGANISM: Homo sapiens
<220> FEATURE:
<223> OTHER INFORMATION: Residues 124-132 of the TADG-14 protein

<400> SEQUENCE: 25

Leu Gln Leu Arg Asp Gln Ala Ser Leu
1               5

<210> SEQ ID NO 26
<211> LENGTH: 9
<212> TYPE: PRT
<213> ORGANISM: Homo sapiens
<220> FEATURE:
<223> OTHER INFORMATION: Residues 170-178 of the TADG-14 protein

<400> SEQUENCE: 26

Thr Leu Asn Cys Ala Glu Val Lys Ile
1               5

<210> SEQ ID NO 27
<211> LENGTH: 9
<212> TYPE: PRT
<213> ORGANISM: Homo sapiens
<220> FEATURE:
<223> OTHER INFORMATION: Residues 208-216of the TADG-14 protein

<400> SEQUENCE: 27

Cys Gln Gly Asp Ser Gly Gly Pro Leu
1               5

<210> SEQ ID NO 28
<211> LENGTH: 9
<212> TYPE: PRT
<213> ORGANISM: Homo sapiens
<220> FEATURE:
<223> OTHER INFORMATION: Residues 54-62 of the TADG-14 protein

<400> SEQUENCE: 28

Gln Gln Leu Leu Cys Gly Gly Val Leu
1               5

<210> SEQ ID NO 29
<211> LENGTH: 9
<212> TYPE: PRT
<213> ORGANISM: Homo sapiens
<220> FEATURE:
<223> OTHER INFORMATION: Residues 62-70 of the TADG-14 protein

<400> SEQUENCE: 29

Leu Val Gly Gly Asn Trp Val Leu Thr
1               5

<210> SEQ ID NO 30
<211> LENGTH: 9
```

```
<212> TYPE: PRT
<213> ORGANISM: Homo sapiens
<220> FEATURE:
<223> OTHER INFORMATION: Residues 191-199 of the TADG-14 protein

<400> SEQUENCE: 30

Gln Ile Thr Asp Gly Met Val Cys Ala
1               5

<210> SEQ ID NO 31
<211> LENGTH: 9
<212> TYPE: PRT
<213> ORGANISM: Homo sapiens
<220> FEATURE:
<223> OTHER INFORMATION: Residues 173-181 of the TADG-14 protein

<400> SEQUENCE: 31

Cys Ala Glu Val Lys Ile Phe Pro Gln
1               5

<210> SEQ ID NO 32
<211> LENGTH: 9
<212> TYPE: PRT
<213> ORGANISM: Homo sapiens
<220> FEATURE:
<223> OTHER INFORMATION: Residues 83-91 of the TADG-14 protein

<400> SEQUENCE: 32

Leu Gly Asp His Ser Leu Gln Asn Lys
1               5

<210> SEQ ID NO 33
<211> LENGTH: 9
<212> TYPE: PRT
<213> ORGANISM: Homo sapiens
<220> FEATURE:
<223> OTHER INFORMATION: Residues 183-191 of the TADG-14 protein

<400> SEQUENCE: 33

Lys Cys Glu Asp Ala Tyr Pro Gly Gln
1               5

<210> SEQ ID NO 34
<211> LENGTH: 9
<212> TYPE: PRT
<213> ORGANISM: Homo sapiens
<220> FEATURE:
<223> OTHER INFORMATION: Residues 192-200 of the TADG-14 protein

<400> SEQUENCE: 34

Ile Thr Asp Gly Met Val Cys Ala Gly
1               5

<210> SEQ ID NO 35
<211> LENGTH: 9
<212> TYPE: PRT
<213> ORGANISM: Homo sapiens
<220> FEATURE:
<223> OTHER INFORMATION: Residues 71-79 of the TADG-14 protein

<400> SEQUENCE: 35

Ala Ala His Cys Lys Lys Pro Lys Tyr
1               5

<210> SEQ ID NO 36
<211> LENGTH: 9
<212> TYPE: PRT
<213> ORGANISM: Homo sapiens
```

```
<220> FEATURE:
<223> OTHER INFORMATION: Residues 113-121 of the TADG-14 protein

<400> SEQUENCE: 36

Asp Val Glu Asp His Asn His Asp Leu
1               5

<210> SEQ ID NO 37
<211> LENGTH: 9
<212> TYPE: PRT
<213> ORGANISM: Homo sapiens
<220> FEATURE:
<223> OTHER INFORMATION: Residues 229-237 of the TADG-14 protein

<400> SEQUENCE: 37

Gly Ser Asp Pro Cys Gly Arg Ser Asp
1               5

<210> SEQ ID NO 38
<211> LENGTH: 9
<212> TYPE: PRT
<213> ORGANISM: Homo sapiens
<220> FEATURE:
<223> OTHER INFORMATION: Residues 111-119 of the TADG-14 protein

<400> SEQUENCE: 38

Ser Ser Asp Val Glu Asp His Asn His
1               5

<210> SEQ ID NO 39
<211> LENGTH: 9
<212> TYPE: PRT
<213> ORGANISM: Homo sapiens
<220> FEATURE:
<223> OTHER INFORMATION: Residues 28-36 of the TADG-14 protein

<400> SEQUENCE: 39

Ala Gln Glu Asp Lys Val Leu Gly Gly
1               5

<210> SEQ ID NO 40
<211> LENGTH: 9
<212> TYPE: PRT
<213> ORGANISM: Homo sapiens
<220> FEATURE:
<223> OTHER INFORMATION: Residues 217-225 of the TADG-14 protein

<400> SEQUENCE: 40

Val Cys Asp Gly Ala Leu Gln Gly Ile
1               5

<210> SEQ ID NO 41
<211> LENGTH: 9
<212> TYPE: PRT
<213> ORGANISM: Homo sapiens
<220> FEATURE:
<223> OTHER INFORMATION: Residues 241-249 of the TADG-14 protein

<400> SEQUENCE: 41

Val Tyr Thr Asn Ile Cys Arg Tyr Leu
1               5

<210> SEQ ID NO 42
<211> LENGTH: 9
<212> TYPE: PRT
<213> ORGANISM: Homo sapiens
<220> FEATURE:
<223> OTHER INFORMATION: Residues 247-255 of the TADG-14 protein
```

```
<400> SEQUENCE: 42

Arg Tyr Leu Asp Trp Ile Lys Lys Ile
1               5

<210> SEQ ID NO 43
<211> LENGTH: 9
<212> TYPE: PRT
<213> ORGANISM: Homo sapiens
<220> FEATURE:
<223> OTHER INFORMATION: Residues 7-15 of the TADG-14 protein

<400> SEQUENCE: 43

Arg Ala Ala Lys Thr Trp Met Phe Leu
1               5

<210> SEQ ID NO 44
<211> LENGTH: 9
<212> TYPE: PRT
<213> ORGANISM: Homo sapiens
<220> FEATURE:
<223> OTHER INFORMATION: Residues 42-50 of the TADG-14 protein

<400> SEQUENCE: 44

His Ser Gln Pro Trp Gln Ala Ala Leu
1               5

<210> SEQ ID NO 45
<211> LENGTH: 9
<212> TYPE: PRT
<213> ORGANISM: Homo sapiens
<220> FEATURE:
<223> OTHER INFORMATION: Residues 48-56 of the TADG-14 protein

<400> SEQUENCE: 45

Ala Ala Leu Phe Gln Gly Gln Gln Leu
1               5

<210> SEQ ID NO 46
<211> LENGTH: 9
<212> TYPE: PRT
<213> ORGANISM: Homo sapiens
<220> FEATURE:
<223> OTHER INFORMATION: Residues 214-222 of the TADG-14 protein

<400> SEQUENCE: 46

Gly Pro Leu Val Cys Asp Gly Ala Leu
1               5

<210> SEQ ID NO 47
<211> LENGTH: 9
<212> TYPE: PRT
<213> ORGANISM: Homo sapiens
<220> FEATURE:
<223> OTHER INFORMATION: Residues 80-88 of the TADG-14 protein

<400> SEQUENCE: 47

Thr Val Arg Leu Gly Asp His Ser Leu
1               5

<210> SEQ ID NO 48
<211> LENGTH: 9
<212> TYPE: PRT
<213> ORGANISM: Homo sapiens
<220> FEATURE:
<223> OTHER INFORMATION: Residues 5-13 of the TADG-14 protein

<400> SEQUENCE: 48
```

```
Arg Pro Arg Ala Ala Lys Thr Trp Met
1               5

<210> SEQ ID NO 49
<211> LENGTH: 9
<212> TYPE: PRT
<213> ORGANISM: Homo sapiens
<220> FEATURE:
<223> OTHER INFORMATION: Residues 8-16 of the TADG-14 protein

<400> SEQUENCE: 49

Ala Ala Lys Thr Trp Met Phe Leu Leu
1               5

<210> SEQ ID NO 50
<211> LENGTH: 9
<212> TYPE: PRT
<213> ORGANISM: Homo sapiens
<220> FEATURE:
<223> OTHER INFORMATION: Residues 3-11 of the TADG-14 protein

<400> SEQUENCE: 50

Arg Pro Arg Pro Arg Ala Ala Lys Thr
1               5

<210> SEQ ID NO 51
<211> LENGTH: 9
<212> TYPE: PRT
<213> ORGANISM: Homo sapiens
<220> FEATURE:
<223> OTHER INFORMATION: Residues 162-170 of the TADG-14 protein

<400> SEQUENCE: 51

Ser Pro Arg Glu Asn Phe Pro Asp Thr
1               5

<210> SEQ ID NO 52
<211> LENGTH: 9
<212> TYPE: PRT
<213> ORGANISM: Homo sapiens
<220> FEATURE:
<223> OTHER INFORMATION: Residues 188-196 of the TADG-14 protein

<400> SEQUENCE: 52

Tyr Pro Gly Gln Ile Thr Asp Gly Met
1               5

<210> SEQ ID NO 53
<211> LENGTH: 9
<212> TYPE: PRT
<213> ORGANISM: Homo sapiens
<220> FEATURE:
<223> OTHER INFORMATION: Residues 133-141 of the TADG-14 protein

<400> SEQUENCE: 53

Gly Ser Lys Val Lys Pro Ile Ser Leu
1               5

<210> SEQ ID NO 54
<211> LENGTH: 9
<212> TYPE: PRT
<213> ORGANISM: Homo sapiens
<220> FEATURE:
<223> OTHER INFORMATION: Residues 73-81 of the TADG-14 protein

<400> SEQUENCE: 54

His Cys Lys Lys Pro Lys Tyr Thr Val
```

```
<210> SEQ ID NO 55
<211> LENGTH: 9
<212> TYPE: PRT
<213> ORGANISM: Homo sapiens
<220> FEATURE:
<223> OTHER INFORMATION: Residues 179-187 of the TADG-14 protein

<400> SEQUENCE: 55

Phe Pro Gln Lys Lys Cys Glu Asp Ala
1               5

<210> SEQ ID NO 56
<211> LENGTH: 9
<212> TYPE: PRT
<213> ORGANISM: Homo sapiens
<220> FEATURE:
<223> OTHER INFORMATION: Residues 234-242 of the TADG-14 protein

<400> SEQUENCE: 56

Gly Arg Ser Asp Lys Pro Gly Val Tyr
1               5

<210> SEQ ID NO 57
<211> LENGTH: 9
<212> TYPE: PRT
<213> ORGANISM: Homo sapiens
<220> FEATURE:
<223> OTHER INFORMATION: Residues 246-254 of the TADG-14 protein

<400> SEQUENCE: 57

Cys Arg Tyr Leu Asp Trp Ile Lys Lys
1               5

<210> SEQ ID NO 58
<211> LENGTH: 9
<212> TYPE: PRT
<213> ORGANISM: Homo sapiens
<220> FEATURE:
<223> OTHER INFORMATION: Residues 101-109 of the TADG-14 protein

<400> SEQUENCE: 58

Val Gln Ser Ile Pro His Pro Cys Tyr
1               5

<210> SEQ ID NO 59
<211> LENGTH: 9
<212> TYPE: PRT
<213> ORGANISM: Homo sapiens
<220> FEATURE:
<223> OTHER INFORMATION: Residues 43-51 of the TADG-14 protein

<400> SEQUENCE: 59

Ser Gln Pro Trp Gln Ala Ala Leu Phe
1               5

<210> SEQ ID NO 60
<211> LENGTH: 9
<212> TYPE: PRT
<213> ORGANISM: Homo sapiens
<220> FEATURE:
<223> OTHER INFORMATION: Residues 6-14 of the TADG-14 protein

<400> SEQUENCE: 60

Pro Arg Ala Ala Lys Thr Trp Met Phe
1               5
```

```
<210> SEQ ID NO 61
<211> LENGTH: 9
<212> TYPE: PRT
<213> ORGANISM: Homo sapiens
<220> FEATURE:
<223> OTHER INFORMATION: Residues 26-34 of the TADG-14 protein

<400> SEQUENCE: 61

Ser Arg Ala Gln Glu Asp Lys Val Leu
1               5

<210> SEQ ID NO 62
<211> LENGTH: 9
<212> TYPE: PRT
<213> ORGANISM: Homo sapiens
<220> FEATURE:
<223> OTHER INFORMATION: Residues 126-134 of the TADG-14 protein

<400> SEQUENCE: 62

Leu Arg Asp Gln Ala Ser Leu Gly Ser
1               5

<210> SEQ ID NO 63
<211> LENGTH: 9
<212> TYPE: PRT
<213> ORGANISM: Homo sapiens
<220> FEATURE:
<223> OTHER INFORMATION: Residues 149-157 of the TADG-14 protein

<400> SEQUENCE: 63

Gly Gln Lys Cys Thr Val Ser Gly Trp
1               5

<210> SEQ ID NO 64
<211> LENGTH: 9
<212> TYPE: PRT
<213> ORGANISM: Homo sapiens
<220> FEATURE:
<223> OTHER INFORMATION: Residues 96-104 of the TADG-14 protein

<400> SEQUENCE: 64

Gln Glu Ile Pro Val Val Gln Ser Ile
1               5

<210> SEQ ID NO 65
<211> LENGTH: 9
<212> TYPE: PRT
<213> ORGANISM: Homo sapiens
<220> FEATURE:
<223> OTHER INFORMATION: Residues 171-179 of the TADG-14 protein

<400> SEQUENCE: 65

Leu Asn Cys Ala Glu Val Lys Ile Phe
1               5

<210> SEQ ID NO 66
<211> LENGTH: 9
<212> TYPE: PRT
<213> ORGANISM: Homo sapiens
<220> FEATURE:
<223> OTHER INFORMATION: Residues 184-192 of the TADG-14 protein

<400> SEQUENCE: 66

Cys Glu Asp Ala Tyr Pro Gly Gln Ile
1               5

<210> SEQ ID NO 67
```

```
<211> LENGTH: 9
<212> TYPE: PRT
<213> ORGANISM: Homo sapiens
<220> FEATURE:
<223> OTHER INFORMATION: Residues 114-122 of the TADG-14 protein

<400> SEQUENCE: 67

Val Glu Asp His Asn His Asp Leu Met
1               5

<210> SEQ ID NO 68
<211> LENGTH: 9
<212> TYPE: PRT
<213> ORGANISM: Homo sapiens
<220> FEATURE:
<223> OTHER INFORMATION: Residues 101-109 of the TADG-14 protein

<400> SEQUENCE: 68

Val Gln Ser Ile Pro His Pro Cys Tyr
1               5

<210> SEQ ID NO 69
<211> LENGTH: 9
<212> TYPE: PRT
<213> ORGANISM: Homo sapiens
<220> FEATURE:
<223> OTHER INFORMATION: Residues 236-244 of the TADG-14 protein

<400> SEQUENCE: 69

Ser Asp Lys Pro Gly Val Tyr Thr Asn
1               5

<210> SEQ ID NO 70
<211> LENGTH: 9
<212> TYPE: PRT
<213> ORGANISM: Homo sapiens
<220> FEATURE:
<223> OTHER INFORMATION: Residues 164-172 of the TADG-14 protein

<400> SEQUENCE: 70

Arg Glu Asn Phe Pro Asp Thr Leu Asn
1               5

<210> SEQ ID NO 71
<211> LENGTH: 9
<212> TYPE: PRT
<213> ORGANISM: Homo sapiens
<220> FEATURE:
<223> OTHER INFORMATION: Residues 174-182 of the TADG-14 protein

<400> SEQUENCE: 71

Ala Glu Val Lys Ile Phe Pro Gln Lys
1               5

<210> SEQ ID NO 72
<211> LENGTH: 1343
<212> TYPE: DNA
<213> ORGANISM: artificial sequence
<220> FEATURE:
<223> OTHER INFORMATION: Anti-sense sequence of TADG-14

<400> SEQUENCE: 72
gaattccgtg agtttattaa gggagatcta gtgcttatcc tagaatcagc          50
ccttgctgcc tatgatcttc ttgatccagt ccaggtagcg gcagatgttg         100
gtatagacgc caggtttgtc ggacctccca caggggtctg agccccagga         150
tgtgatgccc tggagtgcac catcacacac caggggggcct ccagaatcgc        200
```

-continued

```
cctggcacgt gtcagcccct tgctgctgc ctgcacagac catgccatct          250
gtgatctgcc ccgggtaagc atcctcacac ttcttctggg gaaagatttt          300
tacttctgca cagttgagag tgtcaggaaa attctctcgg ggactggtga          350
cagtgcccca gcctgagacg gtgcacttct ggccaggctg ggtgcaatga          400
tctgccaggc tgatgggctt cactttggac cccagggatg cctggtcacg          450
cagttgaaga agcatcagat catggttgtg gtcctccaca tcgctgctgt          500
tgtagcaggg gtgtgggatg gactgaacca caggtatttc ttgctctggg          550
ccatctttat tctgtaggct gtggtctccc aggcgtactg tgtatttcgg          600 tttttttacag tgggcagctg taaggaccca gttgccacct acaaggacac         650
cgccacagag tagttgctgg ccctggaaca aggccgcctg ccaaggctgc          700
gaatggggtt ggcactcatg accccccagc accttgtcct cctgtgccct          750
ggagtgtcct gcccaggctc cccccagcaa gagcaggaac atccacgtct          800
tggccgcacg aggtcggggg cgtcccatgg tgaggtcttc cagaatccag          850
ggcattccct gaaacctatc ctccctgaat ttgcctgttg gaggcccta           900 gttttcccac tgaccaatgt gtaattggga ttcaaagcta tacctgaatt          950
tcctacattt ctagtaacag aatttaccaa acatgaactt tctgatggtg         1000
attacgtaac ttctaatttg aagccctttc ctcatctgtg ttttatgtcc         1050
aagaaatgtc tactgatttt gaaagatttg cttcacattc catcactcag         1100
atctaagttt tttctctcaa gtatggactg ttttatatcc tgtaagagct         1150
gaactacctt gacactggag cctttcttgc ttgctatgat tgaaaatcac         1200
atagaaagga ttcctcataa tcctctagga tggtttcatt tacactgtgt         1250
aaattacaag ccatgacccc ctacattctt acattcataa ggtatttctt         1300
ccatttgagt tcggagagac ttggtaagct ctgcctgcta cag                1343
```

<210> SEQ ID NO 73
<211> LENGTH: 21
<212> TYPE: DNA
<213> ORGANISM: artificial sequence
<220> FEATURE:
<223> OTHER INFORMATION: Sense primer for TADG-14, exon 2 to exon 3

<400> SEQUENCE: 73

```
cgacctcgtg cggccaagac g                                          21
```

<210> SEQ ID NO 74
<211> LENGTH: 21
<212> TYPE: DNA
<213> ORGANISM: artificial sequence
<220> FEATURE:
<223> OTHER INFORMATION: Antisense primer for TADG-14, exon 2 to exon 3

<400> SEQUENCE: 74

```
cagctgtaag gacccagttg c                                          21
```

<210> SEQ ID NO 75
<211> LENGTH: 305
<212> TYPE: PRT
<213> ORGANISM: Homo sapiens
<220> FEATURE:
<223> OTHER INFORMATION: TADG-14 variant protein

<400> SEQUENCE: 75

-continued

```
Met Gly Arg Pro Arg Pro Arg Ala Ala Lys Thr Trp Met Phe Leu
1               5                   10                  15

Leu Leu Leu Gly Gly Ala Trp Ala Ala Cys Gly Ser Leu Asp Leu
                20                  25                  30

Leu Thr Lys Leu Tyr Ala Glu Asn Leu Pro Cys Val His Leu Asn
                35                  40                  45

Pro Gln Trp Pro Ser Gln Pro Ser His Cys Pro Arg Gly Trp Arg
                50                  55                  60

Ser Asn Pro Leu Pro Pro Ala Ala Gly His Ser Arg Ala Gln Glu
                65                  70                  75

Asp Lys Val Leu Gly His Glu Cys Gln Pro His Ser Gln Pro
                80                  85                  90

Trp Gln Ala Ala Leu Phe Gln Gly Gln Gln Leu Leu Cys Gly Gly
                95                  100                 105

Val Leu Val Gly Gly Asn Trp Val Leu Thr Ala Ala His Cys Lys
                110                 115                 120

Lys Pro Lys Tyr Thr Val Arg Leu Gly Asp His Ser Leu Gln Asn
                125                 130                 135

Lys Asp Gly Pro Glu Gln Glu Ile Pro Val Val Gln Ser Ile Pro
                140                 145                 150

His Pro Cys Tyr Asn Ser Ser Asp Val Glu Asp His Asn His Asp
                155                 160                 165

Leu Met Leu Leu Gln Leu Arg Asp Gln Ala Ser Leu Gly Ser Lys
                170                 175                 180

Val Lys Pro Ile Ser Leu Ala Asp His Cys Thr Gln Pro Gly Gln
                185                 190                 195

Lys Cys Thr Val Ser Gly Trp Gly Thr Val Thr Ser Pro Arg Glu
                200                 205                 210

Asn Phe Pro Asp Thr Leu Asn Cys Ala Glu Val Lys Ile Phe Pro
                215                 220                 225

Gln Lys Lys Cys Glu Asp Ala Tyr Pro Gly Gln Ile Thr Asp Gly
                230                 235                 240

Met Val Cys Ala Gly Ser Ser Lys Gly Ala Asp Thr Cys Gln Gly
                245                 250                 255

Asp Ser Gly Gly Pro Leu Val Cys Asp Gly Ala Leu Gln Gly Ile
                260                 265                 270

Thr Ser Trp Gly Ser Asp Pro Cys Gly Arg Ser Asp Lys Pro Gly
                275                 280                 285

Val Tyr Thr Asn Ile Cys Arg Tyr Leu Asp Trp Ile Lys Lys Ile
                290                 295                 300

Ile Gly Ser Lys Gly
                305
```